(12) United States Patent
Sode et al.

(10) Patent No.: US 8,999,691 B2
(45) Date of Patent: Apr. 7, 2015

(54) GLUCOSE DEHYDROGENASE

(75) Inventors: Koji Sode, Tokyo (JP); Kazushige Mori, Tokyo (JP)

(73) Assignee: Ultizyme International Ltd., Tokyo (JP)

(*) Notice: Subject to any disclaimer, the term of this patent is extended or adjusted under 35 U.S.C. 154(b) by 121 days.

(21) Appl. No.: 13/807,637

(22) PCT Filed: Jun. 29, 2011

(86) PCT No.: PCT/JP2011/003741
§ 371 (c)(1),
(2), (4) Date: Mar. 25, 2013

(87) PCT Pub. No.: WO2012/001976
PCT Pub. Date: Jan. 5, 2012

(65) Prior Publication Data
US 2013/0168263 A1    Jul. 4, 2013

(30) Foreign Application Priority Data

Jun. 29, 2010  (JP) ................................. 2010-147799

(51) Int. Cl.
*C12N 9/04*    (2006.01)
*C12Q 1/00*    (2006.01)

(52) U.S. Cl.
CPC .............. *C12N 9/0006* (2013.01); *C12Q 1/006* (2013.01)

(58) Field of Classification Search
None
See application file for complete search history.

(56) References Cited

U.S. PATENT DOCUMENTS

| 6,924,366 B2* | 8/2005 | Stougaard et al. | 536/23.2 |
| 7,494,794 B2* | 2/2009 | Aiba et al. | 435/190 |
| 7,553,649 B2* | 6/2009 | Tsuji et al. | 435/190 |
| 8,691,547 B2* | 4/2014 | Omura et al. | 435/190 |
| 2008/0003628 A1 | 1/2008 | Kitabayashi et al. | |
| 2008/0220460 A1 | 9/2008 | Kawaminami et al. | |
| 2009/0181408 A1 | 7/2009 | Tanaka et al. | |
| 2010/0297743 A1 | 11/2010 | Omura et al. | |
| 2010/0323378 A1* | 12/2010 | Honda et al. | 435/14 |
| 2011/0053194 A1* | 3/2011 | Yuuki et al. | 435/14 |

(Continued)

FOREIGN PATENT DOCUMENTS

| JP | 2007-289148 A | 11/2007 |
| JP | 2008-035747 A | 2/2008 |

(Continued)

OTHER PUBLICATIONS

GenBank Accession No. XP_001584680.1, published Feb. 26, 2008.*

(Continued)

*Primary Examiner* — Rebecca Prouty
*Assistant Examiner* — Richard Ekstrom
(74) *Attorney, Agent, or Firm* — Birch, Stewart, Kolasch & Birch, LLP

(57) ABSTRACT

Disclosed is a modified glucose dehydrogenases that has dramatically increased productivity in *Escherichia coli* and dramatically increased thermal stability, which is obtained by introducing specific amino acid mutations to glucose dehydrogenase derived from *Botryotinia fuckeliana*. Also disclosed is a modified glucose dehydrogenases that has dramatically increased productivity in *E. coli* and dramatically increased thermal stability, which is obtained by replacing two amino acid residues in glucose dehydrogenase of fungal origin with cysteine residues. The novel glucose dehydrogenase has a low reactivity to xylose.

11 Claims, 7 Drawing Sheets

(56) References Cited

U.S. PATENT DOCUMENTS

| | | | |
|---|---|---|---|
| 2012/0122130 A1 | 5/2012 | Omura et al. | |
| 2012/0244565 A1 | 9/2012 | Nishio et al. | |

FOREIGN PATENT DOCUMENTS

| | | | |
|---|---|---|---|
| JP | 2008-035748 A | 2/2008 | |
| JP | 2008-154574 A | 7/2008 | |
| JP | 2008-178380 A | 8/2008 | |
| JP | 2008-237210 A | 10/2008 | |
| JP | 2009/273381 A | 11/2009 | |
| JP | 2011-115156 A | 6/2011 | |
| WO | WO 2004/058958 A1 | 7/2004 | |
| WO | WO 2006/101239 A1 | 9/2006 | |
| WO | WO 2007/011610 A2 | 1/2007 | |
| WO | WO 2007/139013 A1 | 12/2007 | |
| WO | WO 2011/068050 A1 | 6/2011 | |

OTHER PUBLICATIONS

GenBank Accession No. XP_001801353.1, published Apr. 2, 2008.*
GenBank Accession No. XP_001265740.1, published Mar. 26, 2008.*
GenBank Accession No. XP_001273036.1, published Feb. 21, 2008.*
GenBank Accession No. XP_001941385.1, published May 30, 2008.*
GenBank Accession No. CAD88590.1, published Jan. 5, 2004.*
Database UniProt:B8MX95 [Online], "Glucose oxidase, putative; from *Aspergillus flavus*," Mar. 3, 2009, 1 page, XP-002715000.
Extended European Search Report for European Application No. 11800446.4 dated Nov. 4, 2013.
Tsujimura et al., "Novel FAD-Dependent Glucose Dehydrogenase for a Dioxygen-Insensitive Glucose Biosensor," Biosci. Biotechnol. Biochem., vol. 70, No. 3, 2006, pp. 654-659, XP003004577.
Tsujimura et al., "Potential-step coulometry of D-glucose using a novel FAD-dependent glucose dehydrogenase," Anal Bioanal Chem, vol. 386, 2006 (published online Aug. 26, 2006), pp. 645-651, XP0019441071.
International Preliminary Report on Patentability and Written Opinion of the International Searching Authority (Forms PCT/IB/373 and PCT/ISA/237) for International Application No. PCT/JP2011/003741 mailed Feb. 21, 2013.
Database Swiss-Prot [online], Accession No. Q70Q36, <http://www.ncbi.nlm.nih.gov/protein/q70q36>, Oct. 31, 2006 uploaded, [retrieved on Jul. 13, 2011], Rolke Y. et a., Definition: Glucose oxidase.
Rolke et al., "Functional analysis of H2O2-generating systems in *Botrytis cinerea*: the major Cu-Zn-superoxide dismutase (BCS0D1) contributes to virulence on French bean, whereas . . . ," Molecular Plant Pathology (2004), vol. 5, No. 1, pp. 17-27.

* cited by examiner

Fig. 1-1

```
_aln.pos                            10        20        30        40        50
Aspca1_10864             ---MHPPSSKYDFVIVGGGTSGLVVANRLSELNNVTVAVIEVGDSVLNNF
Aspca1_33771             -------MPTYDYIVVGGGTSGLVIANRLTENPDVSVLIIEAGGSVLNNY
Bfu (AJ_555871)          ---MTDSTLNYDYIIVGAGTSGLVIANRLSELN-VTVAVIEAGDSGYNNP
Ssc (XP_001584680)       ---MPELNLAYDYVIVGGGTSGLVIANRLSELN-VTVAVIEAGDLGYENV
40715 (XP_001394544)     ---MDSP-AHYDFVIVGGGTSGLVVANRLSELSDVTVAVIEAGESALNNF
39269 (XP_001391138)     MPSTRLCGPQYDYIVVGGGTSGLVVANRLSENPNVSVLIIEAGGSVLNNS
AoT1 FADGDH              -----MNTTTYDYIVVGGGTSGLVVANRLSENPDVSVLLLEAGASVFNNP _aln.pos                            60        70        80        90       100
Aspca1_10864             NVTDVQGYSLAFNTDIDWAYQTENQTYAGGLKQTIRAGKAIGGTSTINGM
Aspca1_33771             NVTDVDGYGLAFGTDIDWQYETVNQPNAGDLTQTLRAGKALAGTSAINGM
Bfu (AJ_555871)          NVTNPSGYGSAFGTDIDWAYQSINQKYAGNKTQTLRAGKVIGGTSTINGM
Ssc (XP_001584680)       NITNPAGYGLAFGTNIDWAYQSVNQKYAGNATQTLRAGKVIGGTSTINGM
40715 (XP_001394544)     NVSNVMGYSTAFGTEVDWAYQTENQTYAGGLQQTIRAGKALGGTSTINGM
39269 (XP_001391138)     NVTDVNGYGLAFGTDIDWQYETINQSYAGDAPQVLRAGKALSGTSAINGM
AoT1 FADGDH              DVTNANGYGLAFGSAIDWQYQSINQSYAGGKQQVLRAGKALGGTSTINGM _aln.pos                           110       120       130       140       150
Aspca1_10864             SYTRAENAQIDNWERVGNKGWNWKNLLKYYKKSEGFEVPTKDQVAHGASY
Aspca1_33771             AYTRAEDVQIDAWQAIGNEGWTWDSLLPYYLKSENLTAPTASQRAEGATY
Bfu (AJ_555871)          AYTRAEDVQIDAWEAIGNDGWNWANLFPYYKKSQTLEIPTTTQAEAGATY
Ssc (XP_001584680)       AYTRAEDVQIDAWEALGNDGWNWENLFPYYKKSQRLEPPTAAQAESGATY
40715 (XP_001394544)     SYTRAEDVQIDNWEVLGNDGWNWKNLFQYYKKSEGFQVPTKDQIAHGASY
39269 (XP_001391138)     AYTRAEDVQVDAWQTIGNEGWTWDSLFPYYRKSENLTAPTASQRARGATY
AoT1 FADGDH              AYTRAEDVQIDVWQKLGNEGWTWKDLLPYYLKSENLTAPTSSQVAAGAAY _aln.pos                           160       170       180       190       200
Aspca1_10864             NADVHGKDGPLKVGWPTAMTN-GSVFTVLNETMEHLGIHYNPDANSGKMV
Aspca1_33771             DADVNGEDGPLSVGWP-DLPV-GNLTTLLNETFEGLGVPWTEDVNGGKMR
Bfu (AJ_555871)          DASANGFDGPLKVGWLNSLEDTNNFHTTLNDTYAALGVPSNDDVNTGKMV
Ssc (XP_001584680)       DPSANGVDGPLKVGWLNNLAN-DDFHITLNDTYASLGVFANEDVNTGRMV
40715 (XP_001394544)     NASYHGLNGPLKVGWPNSMTN-SSVFPVLEQTFEKLGVQYNPDSEGGKMV
39269 (XP_001391138)     DPSANGEEGPLSVAWP-DIPA-NNLTNTLNATFQGLGVPWTEDVNGGKMR
AoT1 FADGDH              NPAVNGKEGPLKVGWSGSLAS-GNLSVALNRTFQAAGVPWVEDVNGGKMR
```

Fig. 1-2

```
_aln.pos                        210       220       230       240       250
Aspca1_10864             GFTTHPDTLDRDNNVREDAARAYYWPYETRSNLKIISNTQADKIIWSNT-
Aspca1_33771             GLNVFPSTINYTAYVREDAARAYYWPIQSRPNLHLLLDTFANRLVWSDEE
Bfu (AJ_555871)          GYSRYPATYDSALNVRHDAGRAYYYPIANRTNLHLYPNTLAQRITWKSN-
Ssc (XP_001584680)       GHNRYPATYDSTLNVRHDAGRAYYYPIANRTNLHLYPNTMAQRLTWKSG-
40715 (XP_001394544)     GFTVHPDTLDREMNVREDAARAYYWPYEARSNLKIISNTRANKVIWANT-
39269 (XP_001391138)     GFNVYPSTIDYTAYVREDAARAYYWPIASRPNLHLMLDTFVNRLVWKNGG
AoT1 FADGDH              GFNIYPSTLDVDLNVREDAARAYYFPYDDRKNLHLLENTTANRLFWKNG- _aln.pos                        260       270       280       290       300
Aspca1_10864             THGDAIATGIEVTGPYGKET--IYASNEVILSAGALRSPALLELSGIGNP
Aspca1_33771             SEGNITAAGVEITSANGTVS-VIDASQEVIVSAGALKSPAILELSGIGNP
Bfu (AJ_555871)          -TDTPTANGIEVLPNDSSTPYTIYANSEVILSAGALASPLLLELSGIGNP
Ssc (XP_001584680)       -ADIPTTNGVEVLANNSSIPYTISANSEVILSAGALASPLLLELSGIGNP
40715 (XP_001394544)     TQGEAVAVGIEVTNAYGTET---IYADKEVILSAGALRSPAILELSGIGNP
39269 (XP_001391138)     SQGNATAAGVEITSSNGTIS-VIGASQEVIISAGSLKSPGILELSGIGNR
AoT1 FADGDH              SAEEAIADGVEITSADGKVT-RVHAKKEVIISAGALRSPLILELSGVGNP _aln.pos                        310       320       330       340       350
Aspca1_10864             DILQKHNIQVKVNIPTVGENLQDQTNNAFAWESNG--LLTGLATFSALTS
Aspca1_33771             AILEKYNITVKVDLPTVGENLQDQTNTGMYAATAS--GLTGG-KVVIYPN
Bfu (AJ_555871)          SILNEHNISVVVDLPTVGENLQDQTNTGLAYNSSGNTSFSGAGTLVAYPS
Ssc (XP_001584680)       SILNKYNIPVVVDLPTVGENLQDQTNNGLAYTVSEDASFSGVGTLVAYPS
40715 (XP_001394544)     DVLNKHNIPVKVNITTVGENLQDQTNNALSWEGVD--TLTGLATFSVLPS
39269 (XP_001391138)     DILERYNISVRVDLPTVGENLQDQTNAGLGASTTP--GLTGT-KTVVYPN
AoT1 FADGDH              TILKKNNITPRVDLPTVGENLQDQFNNGMAGEGYG--VLAGA-STVTYPS _aln.pos                        360       370       380       390       400
Aspca1_10864             VDQLYGEDVSALAASINATLTTYAKAVYNASNGAVNETNLLEAFNLQYDL
Aspca1_33771             VTDVYGNETSAVAASVRSQLQQWANETAAVSSGTMSAEVLEALFEVQYDL
Bfu (AJ_555871)          AAQVFGSEVQNISAHVLQSLPSYAEQVSAASGNITKATDLLEFFKVQHDL
Ssc (XP_001584680)       AAQVFGSEIQNISTHVLDSLPSYAAQVSAASGNITKAADLLEFFKIQYDL
40715 (XP_001394544)     VNQLYGDNVTALASYVKSQLASYAKTVASASNGAVKEANLVEAFERQYDL
39269 (XP_001391138)     VYDVFGNDTLAVAQSVRRQLKQWANETAQVSSGTMKAEDLEALFQLQYDL
AoT1 FADGDH              ISDVFGNETDSIVASLRSQLSDYAAATVKVSNGHMKQEDLERLYQLQFDL
```

Fig. 1-3

```
_aln.pos                      410       420       430       440       450
Aspca1_10864          IFNS--QVPYAEIVFAP-SGESFNVEYWPLQPFSRGSVHITSANASDLPA
Aspca1_33771          IFKS--QIPIAEILYYPGGTDSLSAQFWALLPFARGNVHIDSADPTAYPS
Bfu (AJ_555871)       IFSTTHPVPMAEILIIP-SATSFSSEYWALLPFARGSIHITSSVACEPAA
Ssc (XP_001584680)    IFSSTHPIPMAEILVMP-STTGFTTEYWALLPFARGNIHITSSIPGTPAA
40715 (XP_001394544)  IFNS--QVPYTEVVFAP-SGNSFAVEYWPLLPFSRGSVHIQSANASDYPA
39269 (XP_001391138)  IFKD--KITIAEILYYPGSTSSISAQYWALMPFARGHVHIASADPTAKPV
AoT1 FADGDH           IVKD--KVPIAEILFHPGGGNAVSSEFWGLLPFARGNIHISSNDPTAPAA _aln.pos                      460       470       480       490       500
Aspca1_10864          INPNYFMFEQDVSAQIDVARYIRKALGTAPLSGIVGDEVSPGLSLLPANS
Aspca1_33771          INPNYYKFDWDLDSQIEVAKYIRKTFQSAPLSEIVQEETTPGFSDVPVDA
Bfu (AJ_555871)       INPNYYMFDWDITSQISTAKFIRSVFETSPFSSFVGSETKPGLNTVSANA
Ssc (XP_001584680)    INPNYYMLDWDITSQFTTAKFIRSIYATSPLSNLVGSETKPGLETVSANA
40715 (XP_001394544)  INPNYFMFDQDAEAQVTVAQYIRKALGTAPLNSLVGEEVSPGLDVLPASA
39269 (XP_001391138)  INPNYYKFDWDLTSQIAVAKYVRKTFQSAPLANIIAEETNPGFEAVAANG
AoT1 FADGDH           INPNYFMFEWDGKSQAGIAKYIRKILRSAPLNKLIAKETKPGLSEIPATA _aln.pos                      510       520       530       540       550
Aspca1_10864          TDSAWNDWVVAHYRPNYHPVGTASMLPREKGGVVDTELRVYGTKNVRVVD
Aspca1_33771          SEEVWTEWLFTQYRSNFHPVGTAIMMPQEKGGVVNTKNVVYGTRNVRVVD
Bfu (AJ_555871)       TEAEWFDWVKTAYRSNFHPVSTAAMMPREVGGVVDSKLKVYGTANVRVVD
Ssc (XP_001584680)    TEAEWSEWIKAGYRSNFHPVSTAAMMPREVGGVVDSRLKVYGTSNVRVVD
40715 (XP_001394544)  SSATWTKWVKENYRTNYHPVGTTSMLPREKGGVVSPELKVYGTKNVRVVD
39269 (XP_001391138)  SEEDWKAWLLTQYRSNFHPVGTAAMMPQDKGGVVNDRLTVYGTSNVRVVD
AoT1 FADGDH           ADEKWVEWLKANYRSNFHPVGTAAMMPRSIGGVVDNRLRVYGTSNVRVVD _aln.pos                      560       570       580
Aspca1_10864          ASVLPFQLSGHLTSTLYAVAEKASDLIKSSYYTV       (SEQ ID NO:5)
Aspca1_33771          ASVLPFQVCGHLVSTLYAAAERTADQIKADSSLF       (SEQ ID NO:6)
Bfu (AJ_555871)       ASILPMQVSGHLVSTLYAVAERAADLIKEDI---       (SEQ ID NO:2)
Ssc (XP_001584680)    ASILPMQVCGHLVSTLYAVAERAADLIKEEI---       (SEQ ID NO:7)
40715 (XP_001394544)  ASVLPFQLCGHLTSTLYAVAERASDLIKESY---       (SEQ ID NO:8)
39269 (XP_001391138)  ASVLPFQVCGHLVSTLYAVAERASDLIKADSALF       (SEQ ID NO:9)
AoT1 FADGDH           ASVLPFQVCGHLVSTLYAVAERASDLIKEDAKSA       (SEQ ID NO:4)
```

SEQUENCE LISTING

<160> NUMBER OF SEQ ID NOS: 9

<210> SEQ ID NO 1
<211> LENGTH: 590
<212> TYPE: PRT
<213> ORGANISM: Botryothinia fuckeliana

<400> SEQUENCE: 1

Met Tyr Arg Leu Leu Ser Thr Phe Ala Val Ala Ser Leu Ala Ala Ala
1               5                   10                  15

Ser Thr Asp Ser Thr Leu Asn Tyr Asp Tyr Ile Ile Val Gly Ala Gly
            20                  25                  30

Thr Ser Gly Leu Val Ile Ala Asn Arg Leu Ser Glu Leu Asn Val Thr
        35                  40                  45

Val Ala Val Ile Glu Ala Gly Asp Ser Gly Tyr Asn Asn Pro Asn Val
    50                  55                  60

Thr Asn Pro Ser Gly Tyr Gly Ser Ala Phe Gly Thr Asp Ile Asp Trp
65                  70                  75                  80

Ala Tyr Gln Ser Ile Asn Gln Lys Tyr Ala Gly Asn Lys Thr Gln Thr
                85                  90                  95

Leu Arg Ala Gly Lys Val Ile Gly Gly Thr Ser Thr Ile Asn Gly Met
            100                 105                 110

Ala Tyr Thr Arg Ala Glu Asp Val Gln Ile Asp Ala Trp Glu Ala Ile
        115                 120                 125

Gly Asn Asp Gly Trp Asn Trp Ala Asn Leu Phe Pro Tyr Tyr Lys Lys
    130                 135                 140

Ser Gln Thr Leu Glu Ile Pro Thr Thr Gln Ala Glu Ala Gly Ala
145                 150                 155                 160

```
Thr Tyr Asp Ala Ser Ala Asn Gly Phe Asp Gly Pro Leu Lys Val Gly
            165                 170                 175

Trp Leu Asn Ser Leu Glu Asp Thr Asn Asn Phe His Thr Thr Leu Asn
            180                 185                 190

Asp Thr Tyr Ala Ala Leu Gly Val Pro Ser Asn Asp Val Asn Thr
            195                 200                 205

Gly Lys Met Val Gly Tyr Ser Arg Tyr Pro Ala Thr Tyr Asp Ser Ala
            210                 215                 220

Leu Asn Val Arg His Asp Ala Gly Arg Ala Tyr Tyr Pro Ile Ala
225                 230                 235                 240

Asn Arg Thr Asn Leu His Leu Tyr Pro Asn Thr Leu Ala Gln Arg Ile
            245                 250                 255

Thr Trp Lys Ser Asn Thr Asp Thr Pro Thr Ala Asn Gly Ile Glu Val
            260                 265                 270

Leu Pro Asn Asp Ser Ser Thr Pro Tyr Thr Ile Tyr Ala Asn Ser Glu
            275                 280                 285

Val Ile Leu Ser Ala Gly Ala Leu Ala Ser Pro Leu Leu Leu Glu Leu
            290                 295                 300

Ser Gly Ile Gly Asn Pro Ser Ile Leu Asn Glu His Asn Ile Ser Val
305                 310                 315                 320

Val Val Asp Leu Pro Thr Val Gly Glu Asn Leu Gln Asp Gln Thr Asn
            325                 330                 335

Thr Gly Leu Ala Tyr Asn Ser Ser Gly Asn Thr Ser Phe Ser Gly Ala
            340                 345                 350

Gly Thr Leu Val Ala Tyr Pro Ser Ala Ala Gln Val Phe Gly Ser Glu
            355                 360                 365

Val Gln Asn Ile Ser Ala His Val Leu Gln Ser Leu Pro Ser Tyr Ala
            370                 375                 380

Glu Gln Val Ser Ala Ala Ser Gly Asn Ile Thr Lys Ala Thr Asp Leu
385                 390                 395                 400

Leu Glu Phe Phe Lys Val Gln His Asp Leu Ile Phe Ser Thr Thr His
            405                 410                 415

Pro Val Pro Met Ala Glu Ile Leu Ile Ile Pro Ser Ala Thr Ser Phe
            420                 425                 430

Ser Ser Glu Tyr Trp Ala Leu Leu Pro Phe Ala Arg Gly Ser Ile His
            435                 440                 445

Ile Thr Ser Ser Val Ala Gly Glu Pro Ala Ala Ile Asn Pro Asn Tyr
            450                 455                 460

Tyr Met Phe Asp Trp Asp Ile Thr Ser Gln Ile Ser Thr Ala Lys Phe
465                 470                 475                 480

Ile Arg Ser Val Phe Glu Thr Ser Pro Phe Ser Ser Phe Val Gly Ser
            485                 490                 495

Glu Thr Lys Pro Gly Leu Asn Thr Val Ser Ala Asn Ala Thr Glu Ala
            500                 505                 510

Glu Trp Phe Asp Trp Val Lys Thr Ala Tyr Arg Ser Asn Phe His Pro
            515                 520                 525

Val Ser Thr Ala Ala Met Met Pro Arg Glu Val Gly Gly Val Val Asp
            530                 535                 540

Ser Lys Leu Lys Val Tyr Gly Thr Ala Asn Val Arg Val Val Asp Ala
545                 550                 555                 560

Ser Ile Leu Pro Met Gln Val Ser Gly His Leu Val Ser Thr Leu Tyr
            565                 570                 575

Ala Val Ala Glu Arg Ala Ala Asp Leu Ile Lys Glu Asp Ile
```

580             585             590

<210> SEQ ID NO 2
<211> LENGTH: 574
<212> TYPE: PRT
<213> ORGANISM: Botryothinia fuckeliana

<400> SEQUENCE: 2

Met Thr Asp Ser Thr Leu Asn Tyr Asp Tyr Ile Ile Val Gly Ala Gly
1               5                   10                  15

Thr Ser Gly Leu Val Ile Ala Asn Arg Leu Ser Glu Leu Asn Val Thr
            20                  25                  30

Val Ala Val Ile Glu Ala Gly Asp Ser Gly Tyr Asn Asn Pro Asn Val
        35                  40                  45

Thr Asn Pro Ser Gly Tyr Gly Ser Ala Phe Gly Thr Asp Ile Asp Trp
    50                  55                  60

Ala Tyr Gln Ser Ile Asn Gln Lys Tyr Ala Gly Asn Lys Thr Gln Thr
65              70                  75                  80

Leu Arg Ala Gly Lys Val Ile Gly Gly Thr Ser Thr Ile Asn Gly Met
            85                  90                  95

Ala Tyr Thr Arg Ala Glu Asp Val Gln Ile Asp Ala Trp Glu Ala Ile
        100                 105                 110

Gly Asn Asp Gly Trp Asn Trp Ala Asn Leu Phe Pro Tyr Tyr Lys Lys
    115                 120                 125

Ser Gln Thr Leu Glu Ile Pro Thr Thr Thr Gln Ala Glu Ala Gly Ala
130                 135                 140

Thr Tyr Asp Ala Ser Ala Asn Gly Phe Asp Gly Pro Leu Lys Val Gly
145                 150                 155                 160

Trp Leu Asn Ser Leu Glu Asp Thr Asn Asn Phe His Thr Thr Leu Asn
                165                 170                 175

Asp Thr Tyr Ala Ala Leu Gly Val Pro Ser Asn Asp Asp Val Asn Thr
            180                 185                 190

Gly Lys Met Val Gly Tyr Ser Arg Tyr Pro Ala Thr Tyr Asp Ser Ala
        195                 200                 205

Leu Asn Val Arg His Asp Ala Gly Arg Ala Tyr Tyr Tyr Pro Ile Ala
    210                 215                 220

Asn Arg Thr Asn Leu His Leu Tyr Pro Asn Thr Leu Ala Gln Arg Ile
225                 230                 235                 240

Thr Trp Lys Ser Asn Thr Asp Thr Pro Thr Ala Asn Gly Ile Glu Val
                245                 250                 255

Leu Pro Asn Asp Ser Ser Thr Pro Tyr Thr Ile Tyr Ala Asn Ser Glu
            260                 265                 270

Val Ile Leu Ser Ala Gly Ala Leu Ala Ser Pro Leu Leu Leu Glu Leu
        275                 280                 285

Ser Gly Ile Gly Asn Pro Ser Ile Leu Asn Glu His Asn Ile Ser Val
    290                 295                 300

Val Val Asp Leu Pro Thr Val Gly Glu Asn Leu Gln Asp Gln Thr Asn
305                 310                 315                 320

Thr Gly Leu Ala Tyr Asn Ser Ser Gly Asn Thr Ser Phe Ser Gly Ala
                325                 330                 335

Gly Thr Leu Val Ala Tyr Pro Ser Ala Ala Gln Val Phe Gly Ser Glu
            340                 345                 350

Val Gln Asn Ile Ser Ala His Val Leu Gln Ser Leu Pro Ser Tyr Ala
        355                 360                 365

Glu Gln Val Ser Ala Ala Ser Gly Asn Ile Thr Lys Ala Thr Asp Leu
    370                 375                 380

Leu Glu Phe Phe Lys Val Gln His Asp Leu Ile Phe Ser Thr Thr His
385                 390                 395                 400

Pro Val Pro Met Ala Glu Ile Leu Ile Ile Pro Ser Ala Thr Ser Phe
                405                 410                 415

Ser Ser Glu Tyr Trp Ala Leu Leu Pro Phe Ala Arg Gly Ser Ile His
            420                 425                 430

Ile Thr Ser Ser Val Ala Gly Glu Pro Ala Ala Ile Asn Pro Asn Tyr
        435                 440                 445

Tyr Met Phe Asp Trp Asp Ile Thr Ser Gln Ile Ser Thr Ala Lys Phe
450                 455                 460

Ile Arg Ser Val Phe Glu Thr Ser Pro Phe Ser Ser Phe Val Gly Ser
465                 470                 475                 480

Glu Thr Lys Pro Gly Leu Asn Thr Val Ser Ala Asn Ala Thr Glu Ala
                485                 490                 495

Glu Trp Phe Asp Trp Val Lys Thr Ala Tyr Arg Ser Asn Phe His Pro
            500                 505                 510

Val Ser Thr Ala Ala Met Met Pro Arg Glu Val Gly Gly Val Val Asp
        515                 520                 525

Ser Lys Leu Lys Val Tyr Gly Thr Ala Asn Val Arg Val Val Asp Ala
530                 535                 540

Ser Ile Leu Pro Met Gln Val Ser Gly His Leu Val Ser Thr Leu Tyr
545                 550                 555                 560

Ala Val Ala Glu Arg Ala Ala Asp Leu Ile Lys Glu Asp Ile
                565                 570

<210> SEQ ID NO 3
<211> LENGTH: 593
<212> TYPE: PRT
<213> ORGANISM: Aspergillus oryzae

<400> SEQUENCE: 3

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Leu Glu Ala Gly Ala Ser Val Phe
50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
130                 135                 140

Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
                165                 170                 175

Pro Leu Lys Val Gly Trp Ser Gly Ser Leu Ala Ser Gly Asn Leu Ser
        180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
        210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
        260                 265                 270

Asp Gly Val Glu Ile Thr Ser Ala Asp Gly Lys Val Thr Arg Val His
        275                 280                 285

Ala Lys Lys Glu Val Ile Ile Ser Ala Gly Ala Leu Arg Ser Pro Leu
        290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Glu Gly Tyr Gly Val Leu Ala
                340                 345                 350

Gly Ala Ser Thr Val Thr Tyr Pro Ser Ile Ser Asp Val Phe Gly Asn
        355                 360                 365

Glu Thr Asp Ser Ile Val Ala Ser Leu Arg Ser Gln Leu Ser Asp Tyr
        370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
                405                 410                 415

Val Pro Ile Ala Glu Ile Leu Phe His Pro Gly Gly Gly Asn Ala Val
        420                 425                 430

Ser Ser Glu Phe Trp Gly Leu Leu Pro Phe Ala Arg Gly Asn Ile His
        435                 440                 445

Ile Ser Ser Asn Asp Pro Thr Ala Pro Ala Ala Ile Asn Pro Asn Tyr
450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
                485                 490                 495

Glu Thr Lys Pro Gly Leu Ser Glu Ile Pro Ala Thr Ala Ala Asp Glu
        500                 505                 510

Lys Trp Val Glu Trp Leu Lys Ala Asn Tyr Arg Ser Asn Phe His Pro
        515                 520                 525

Val Gly Thr Ala Ala Met Met Pro Arg Ser Ile Gly Gly Val Val Asp
        530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
                565                 570                 575

Ala Val Ala Glu Arg Ala Ser Asp Leu Ile Lys Glu Asp Ala Lys Ser
        580                 585                 590

Ala

<210> SEQ ID NO 4
<211> LENGTH: 571
<212> TYPE: PRT
<213> ORGANISM: Aspergillus oryzae

<400> SEQUENCE: 4

```
Met Asn Thr Thr Thr Tyr Asp Tyr Ile Val Val Gly Gly Thr Ser
1               5                   10                  15

Gly Leu Val Val Ala Asn Arg Leu Ser Glu Asn Pro Asp Val Ser Val
            20                  25                  30

Leu Leu Leu Glu Ala Gly Ala Ser Val Phe Asn Asn Pro Asp Val Thr
        35                  40                  45

Asn Ala Asn Gly Tyr Gly Leu Ala Phe Gly Ser Ala Ile Asp Trp Gln
    50                  55                  60

Tyr Gln Ser Ile Asn Gln Ser Tyr Ala Gly Gly Lys Gln Gln Val Leu
65                  70                  75                  80

Arg Ala Gly Lys Ala Leu Gly Gly Thr Ser Thr Ile Asn Gly Met Ala
                85                  90                  95

Tyr Thr Arg Ala Glu Asp Val Gln Ile Asp Val Trp Gln Lys Leu Gly
            100                 105                 110

Asn Glu Gly Trp Thr Trp Lys Asp Leu Leu Pro Tyr Tyr Leu Lys Ser
        115                 120                 125

Glu Asn Leu Thr Ala Pro Thr Ser Ser Gln Val Ala Ala Gly Ala Ala
    130                 135                 140

Tyr Asn Pro Ala Val Asn Gly Lys Glu Gly Pro Leu Lys Val Gly Trp
145                 150                 155                 160

Ser Gly Ser Leu Ala Ser Gly Asn Leu Ser Val Ala Leu Asn Arg Thr
                165                 170                 175

Phe Gln Ala Ala Gly Val Pro Trp Val Glu Asp Val Asn Gly Gly Lys
            180                 185                 190

Met Arg Gly Phe Asn Ile Tyr Pro Ser Thr Leu Asp Val Asp Leu Asn
        195                 200                 205

Val Arg Glu Asp Ala Ala Arg Ala Tyr Tyr Phe Pro Tyr Asp Asp Arg
    210                 215                 220

Lys Asn Leu His Leu Leu Glu Asn Thr Thr Ala Asn Arg Leu Phe Trp
225                 230                 235                 240

Lys Asn Gly Ser Ala Glu Glu Ala Ile Ala Asp Gly Val Glu Ile Thr
                245                 250                 255

Ser Ala Asp Gly Lys Val Thr Arg Val His Ala Lys Lys Glu Val Ile
            260                 265                 270

Ile Ser Ala Gly Ala Leu Arg Ser Pro Leu Ile Leu Glu Leu Ser Gly
        275                 280                 285

Val Gly Asn Pro Thr Ile Leu Lys Lys Asn Asn Ile Thr Pro Arg Val
    290                 295                 300

Asp Leu Pro Thr Val Gly Glu Asn Leu Gln Asp Gln Phe Asn Asn Gly
305                 310                 315                 320

Met Ala Gly Glu Gly Tyr Gly Val Leu Ala Gly Ala Ser Thr Val Thr
                325                 330                 335

Tyr Pro Ser Ile Ser Asp Val Phe Gly Asn Glu Thr Asp Ser Ile Val
            340                 345                 350

Ala Ser Leu Arg Ser Gln Leu Ser Asp Tyr Ala Ala Ala Thr Val Lys
        355                 360                 365
```

```
Val Ser Asn Gly His Met Lys Gln Glu Asp Leu Glu Arg Leu Tyr Gln
    370                 375                 380

Leu Gln Phe Asp Leu Ile Val Lys Asp Lys Val Pro Ile Ala Glu Ile
385                 390                 395                 400

Leu Phe His Pro Gly Gly Asn Ala Val Ser Ser Glu Phe Trp Gly
                405                 410                 415

Leu Leu Pro Phe Ala Arg Gly Asn Ile His Ile Ser Ser Asn Asp Pro
            420                 425                 430

Thr Ala Pro Ala Ala Ile Asn Pro Asn Tyr Phe Met Phe Glu Trp Asp
            435                 440                 445

Gly Lys Ser Gln Ala Gly Ile Ala Lys Tyr Ile Arg Lys Ile Leu Arg
450                 455                 460

Ser Ala Pro Leu Asn Lys Leu Ile Ala Lys Glu Thr Lys Pro Gly Leu
465                 470                 475                 480

Ser Glu Ile Pro Ala Thr Ala Asp Glu Lys Trp Val Glu Trp Leu
                485                 490                 495

Lys Ala Asn Tyr Arg Ser Asn Phe His Pro Val Gly Thr Ala Ala Met
            500                 505                 510

Met Pro Arg Ser Ile Gly Gly Val Val Asp Asn Arg Leu Arg Val Tyr
            515                 520                 525

Gly Thr Ser Asn Val Arg Val Val Asp Ala Ser Val Leu Pro Phe Gln
530                 535                 540

Val Cys Gly His Leu Val Ser Thr Leu Tyr Ala Val Ala Glu Arg Ala
545                 550                 555                 560

Ser Asp Leu Ile Lys Glu Asp Ala Lys Ser Ala
                565                 570

<210> SEQ ID NO 5
<211> LENGTH: 572
<212> TYPE: PRT
<213> ORGANISM: Aspergillus carbonarius

<400> SEQUENCE: 5

Met His Pro Pro Ser Ser Lys Tyr Asp Phe Ile Val Gly Gly Gly
1               5                   10                  15

Thr Ser Gly Leu Val Val Ala Asn Arg Leu Ser Glu Leu Asn Asn Val
            20                  25                  30

Thr Val Ala Val Ile Glu Val Gly Asp Ser Val Leu Asn Asn Phe Asn
        35                  40                  45

Val Thr Asp Val Gln Gly Tyr Ser Leu Ala Phe Asn Thr Asp Ile Asp
50                  55                  60

Trp Ala Tyr Gln Thr Glu Asn Gln Thr Tyr Ala Gly Gly Leu Lys Gln
65                  70                  75                  80

Thr Ile Arg Ala Gly Lys Ala Ile Gly Gly Thr Ser Thr Ile Asn Gly
                85                  90                  95

Met Ser Tyr Thr Arg Ala Glu Asn Ala Gln Ile Asp Asn Trp Glu Arg
            100                 105                 110

Val Gly Asn Lys Gly Trp Asn Trp Lys Asn Leu Leu Lys Tyr Tyr Lys
        115                 120                 125

Lys Ser Glu Gly Phe Glu Val Pro Thr Lys Asp Gln Val Ala His Gly
    130                 135                 140

Ala Ser Tyr Asn Ala Asp Val His Gly Lys Asp Gly Pro Leu Lys Val
145                 150                 155                 160

Gly Trp Pro Thr Ala Met Thr Asn Gly Ser Val Phe Thr Val Leu Asn
                165                 170                 175
```

-continued

```
Glu Thr Met Glu His Leu Gly Ile His Tyr Asn Pro Asp Ala Asn Ser
            180                 185                 190

Gly Lys Met Val Gly Phe Thr Thr His Pro Asp Thr Leu Asp Arg Asp
        195                 200                 205

Asn Asn Val Arg Glu Asp Ala Arg Ala Tyr Tyr Trp Pro Tyr Glu
210                 215                 220

Thr Arg Ser Asn Leu Lys Ile Ile Ser Asn Thr Gln Ala Asp Lys Ile
225                 230                 235                 240

Ile Trp Ser Asn Thr Thr His Gly Asp Ala Ile Ala Thr Gly Ile Glu
                    245                 250                 255

Val Thr Gly Pro Tyr Gly Lys Glu Thr Ile Tyr Ala Ser Asn Glu Val
            260                 265                 270

Ile Leu Ser Ala Gly Ala Leu Arg Ser Pro Ala Leu Leu Glu Leu Ser
        275                 280                 285

Gly Ile Gly Asn Pro Asp Ile Leu Gln Lys His Asn Ile Gln Val Lys
    290                 295                 300

Val Asn Ile Pro Thr Val Gly Glu Asn Leu Gln Asp Gln Thr Asn Asn
305                 310                 315                 320

Ala Phe Ala Trp Glu Ser Asn Gly Leu Leu Thr Gly Leu Ala Thr Phe
                    325                 330                 335

Ser Ala Leu Thr Ser Val Asp Gln Leu Tyr Gly Glu Asp Val Ser Ala
            340                 345                 350

Leu Ala Ala Ser Ile Asn Ala Thr Leu Thr Thr Tyr Ala Lys Ala Val
        355                 360                 365

Tyr Asn Ala Ser Asn Gly Ala Val Asn Glu Thr Asn Leu Leu Glu Ala
    370                 375                 380

Phe Asn Leu Gln Tyr Asp Leu Ile Phe Asn Ser Gln Val Pro Tyr Ala
385                 390                 395                 400

Glu Ile Val Phe Ala Pro Ser Gly Glu Ser Phe Asn Val Glu Tyr Trp
                    405                 410                 415

Pro Leu Gln Pro Phe Ser Arg Gly Ser Val His Ile Thr Ser Ala Asn
            420                 425                 430

Ala Ser Asp Leu Pro Ala Ile Asn Pro Asn Tyr Phe Met Phe Glu Gln
        435                 440                 445

Asp Val Ser Ala Gln Ile Asp Val Ala Arg Tyr Ile Arg Lys Ala Leu
    450                 455                 460

Gly Thr Ala Pro Leu Ser Gly Ile Val Gly Asp Glu Val Ser Pro Gly
465                 470                 475                 480

Leu Ser Leu Leu Pro Ala Asn Ser Thr Asp Ser Ala Trp Asn Asp Trp
                    485                 490                 495

Val Val Ala His Tyr Arg Pro Asn Tyr His Pro Val Gly Thr Ala Ser
            500                 505                 510

Met Leu Pro Arg Glu Lys Gly Gly Val Val Asp Thr Glu Leu Arg Val
        515                 520                 525

Tyr Gly Thr Lys Asn Val Arg Val Val Asp Ala Ser Val Leu Pro Phe
    530                 535                 540

Gln Leu Ser Gly His Leu Thr Ser Thr Leu Tyr Ala Val Ala Glu Lys
545                 550                 555                 560

Ala Ser Asp Leu Ile Lys Ser Ser Tyr Tyr Thr Val
                    565                 570
```

<210> SEQ ID NO 6
<211> LENGTH: 569

<212> TYPE: PRT
<213> ORGANISM: Aspergillus carbonarius

<400> SEQUENCE: 6

```
Met Pro Thr Tyr Asp Tyr Ile Val Val Gly Gly Thr Ser Gly Leu
1               5                   10                  15

Val Ile Ala Asn Arg Leu Thr Glu Asn Pro Asp Val Ser Val Leu Ile
            20                  25                  30

Ile Glu Ala Gly Gly Ser Val Leu Asn Asn Tyr Asn Val Thr Asp Val
        35                  40                  45

Asp Gly Tyr Gly Leu Ala Phe Gly Thr Asp Ile Asp Trp Gln Tyr Glu
    50                  55                  60

Thr Val Asn Gln Pro Asn Ala Gly Asp Leu Thr Gln Thr Leu Arg Ala
65                  70                  75                  80

Gly Lys Ala Leu Ala Gly Thr Ser Ala Ile Asn Gly Met Ala Tyr Thr
                85                  90                  95

Arg Ala Glu Asp Val Gln Ile Asp Ala Trp Gln Ala Ile Gly Asn Glu
            100                 105                 110

Gly Trp Thr Trp Asp Ser Leu Leu Pro Tyr Tyr Leu Lys Ser Glu Asn
        115                 120                 125

Leu Thr Ala Pro Thr Ala Ser Gln Arg Ala Glu Gly Ala Thr Tyr Asp
130                 135                 140

Ala Asp Val Asn Gly Glu Asp Gly Pro Leu Ser Val Gly Trp Pro Asp
145                 150                 155                 160

Leu Pro Val Gly Asn Leu Thr Thr Leu Leu Asn Glu Thr Phe Glu Gly
                165                 170                 175

Leu Gly Val Pro Trp Thr Glu Asp Val Asn Gly Gly Lys Met Arg Gly
            180                 185                 190

Leu Asn Val Phe Pro Ser Thr Ile Asn Tyr Thr Ala Tyr Val Arg Glu
        195                 200                 205

Asp Ala Ala Arg Ala Tyr Tyr Trp Pro Ile Gln Ser Arg Pro Asn Leu
    210                 215                 220

His Leu Leu Leu Asp Thr Phe Ala Asn Arg Leu Val Trp Ser Asp Glu
225                 230                 235                 240

Glu Ser Glu Gly Asn Ile Thr Ala Ala Gly Val Glu Ile Thr Ser Ala
                245                 250                 255

Asn Gly Thr Val Ser Val Ile Asp Ala Ser Gln Glu Val Ile Val Ser
            260                 265                 270

Ala Gly Ala Leu Lys Ser Pro Ala Ile Leu Glu Leu Ser Gly Ile Gly
        275                 280                 285

Asn Pro Ala Ile Leu Glu Lys Tyr Asn Ile Thr Val Lys Val Asp Leu
    290                 295                 300

Pro Thr Val Gly Glu Asn Leu Gln Asp Gln Thr Asn Thr Gly Met Tyr
305                 310                 315                 320

Ala Ala Thr Ala Ser Gly Leu Thr Gly Gly Lys Val Val Ile Tyr Pro
                325                 330                 335

Asn Val Thr Asp Val Tyr Gly Asn Glu Thr Ser Ala Val Ala Ala Ser
            340                 345                 350

Val Arg Ser Gln Leu Gln Gln Trp Ala Asn Glu Thr Ala Ala Val Ser
        355                 360                 365

Ser Gly Thr Met Ser Ala Glu Val Leu Glu Ala Leu Phe Glu Val Gln
    370                 375                 380

Tyr Asp Leu Ile Phe Lys Ser Gln Ile Pro Ile Ala Glu Ile Leu Tyr
385                 390                 395                 400
```

```
Tyr Pro Gly Gly Thr Asp Ser Leu Ser Ala Gln Phe Trp Ala Leu Leu
                405                 410                 415

Pro Phe Ala Arg Gly Asn Val His Ile Asp Ser Ala Asp Pro Thr Ala
            420                 425                 430

Tyr Pro Ser Ile Asn Pro Asn Tyr Tyr Lys Phe Asp Trp Asp Leu Asp
        435                 440                 445

Ser Gln Ile Glu Val Ala Lys Tyr Ile Arg Lys Thr Phe Gln Ser Ala
    450                 455                 460

Pro Leu Ser Glu Ile Val Gln Glu Glu Thr Thr Pro Gly Phe Ser Asp
465                 470                 475                 480

Val Pro Val Asp Ala Ser Glu Glu Val Trp Thr Glu Trp Leu Phe Thr
                485                 490                 495

Gln Tyr Arg Ser Asn Phe His Pro Val Gly Thr Ala Ile Met Met Pro
            500                 505                 510

Gln Glu Lys Gly Gly Val Val Asn Thr Lys Asn Val Val Tyr Gly Thr
        515                 520                 525

Arg Asn Val Arg Val Val Asp Ala Ser Val Leu Pro Phe Gln Val Cys
    530                 535                 540

Gly His Leu Val Ser Thr Leu Tyr Ala Ala Ala Glu Arg Thr Ala Asp
545                 550                 555                 560

Gln Ile Lys Ala Asp Ser Ser Leu Phe
                565

<210> SEQ ID NO 7
<211> LENGTH: 573
<212> TYPE: PRT
<213> ORGANISM: Sclenotinia sclerotiorum

<400> SEQUENCE: 7

Met Pro Glu Leu Asn Leu Ala Tyr Asp Tyr Val Ile Val Gly Gly Gly
1               5                   10                  15

Thr Ser Gly Leu Val Ile Ala Asn Arg Leu Ser Glu Leu Asn Val Thr
            20                  25                  30

Val Ala Val Ile Glu Ala Gly Asp Leu Gly Tyr Glu Asn Val Asn Ile
        35                  40                  45

Thr Asn Pro Ala Gly Tyr Gly Leu Ala Phe Gly Thr Asn Ile Asp Trp
    50                  55                  60

Ala Tyr Gln Ser Val Asn Gln Lys Tyr Ala Gly Asn Ala Thr Gln Thr
65                  70                  75                  80

Leu Arg Ala Gly Lys Val Ile Gly Gly Thr Ser Thr Ile Asn Gly Met
                85                  90                  95

Ala Tyr Thr Arg Ala Glu Asp Val Gln Ile Asp Ala Trp Glu Ala Leu
            100                 105                 110

Gly Asn Asp Gly Trp Asn Trp Glu Asn Leu Phe Pro Tyr Tyr Lys Lys
        115                 120                 125

Ser Gln Arg Leu Glu Pro Pro Thr Ala Ala Gln Ala Glu Ser Gly Ala
    130                 135                 140

Thr Tyr Asp Pro Ser Ala Asn Gly Val Asp Gly Pro Leu Lys Val Gly
145                 150                 155                 160

Trp Leu Asn Asn Leu Ala Asn Asp Asp Phe His Ile Thr Leu Asn Asp
                165                 170                 175

Thr Tyr Ala Ser Leu Gly Val Phe Ala Asn Glu Asp Val Asn Thr Gly
            180                 185                 190

Arg Met Val Gly His Asn Arg Tyr Pro Ala Thr Tyr Asp Ser Thr Leu
```

```
                195                 200                 205
Asn Val Arg His Asp Ala Gly Arg Ala Tyr Tyr Tyr Pro Ile Ala Asn
210                 215                 220
Arg Thr Asn Leu His Leu Tyr Pro Asn Thr Met Ala Gln Arg Leu Thr
225                 230                 235                 240
Trp Lys Ser Gly Ala Asp Ile Pro Thr Thr Asn Gly Val Glu Val Leu
                245                 250                 255
Ala Asn Asn Ser Ser Ile Pro Tyr Thr Ile Ser Ala Asn Ser Glu Val
            260                 265                 270
Ile Leu Ser Ala Gly Ala Leu Ala Ser Pro Leu Leu Leu Glu Leu Ser
        275                 280                 285
Gly Ile Gly Asn Pro Ser Ile Leu Asn Lys Tyr Asn Ile Pro Val Val
    290                 295                 300
Val Asp Leu Pro Thr Val Gly Glu Asn Leu Gln Asp Gln Thr Asn Asn
305                 310                 315                 320
Gly Leu Ala Tyr Thr Val Ser Glu Asp Ala Ser Phe Ser Gly Val Gly
                325                 330                 335
Thr Leu Val Ala Tyr Pro Ser Ala Ala Gln Val Phe Gly Ser Glu Ile
            340                 345                 350
Gln Asn Ile Ser Thr His Val Leu Asp Ser Leu Pro Ser Tyr Ala Ala
        355                 360                 365
Gln Val Ser Ala Ala Ser Gly Asn Ile Thr Lys Ala Ala Asp Leu Leu
    370                 375                 380
Glu Phe Phe Lys Ile Gln Tyr Asp Leu Ile Phe Ser Ser Thr His Pro
385                 390                 395                 400
Ile Pro Met Ala Glu Ile Leu Val Met Pro Ser Thr Thr Gly Phe Thr
                405                 410                 415
Thr Glu Tyr Trp Ala Leu Leu Pro Phe Ala Arg Gly Asn Ile His Ile
            420                 425                 430
Thr Ser Ser Ile Pro Gly Thr Pro Ala Ala Ile Asn Pro Asn Tyr Tyr
        435                 440                 445
Met Leu Asp Trp Asp Ile Thr Ser Gln Phe Thr Thr Ala Lys Phe Ile
    450                 455                 460
Arg Ser Ile Tyr Ala Thr Ser Pro Leu Ser Asn Leu Val Gly Ser Glu
465                 470                 475                 480
Thr Lys Pro Gly Leu Glu Thr Val Ser Ala Asn Ala Thr Glu Ala Glu
                485                 490                 495
Trp Ser Glu Trp Ile Lys Ala Gly Tyr Arg Ser Asn Phe His Pro Val
            500                 505                 510
Ser Thr Ala Ala Met Met Pro Arg Glu Val Gly Gly Val Val Asp Ser
        515                 520                 525
Arg Leu Lys Val Tyr Gly Thr Ser Asn Val Arg Val Val Asp Ala Ser
    530                 535                 540
Ile Leu Pro Met Gln Val Cys Gly His Leu Val Ser Thr Leu Tyr Ala
545                 550                 555                 560
Val Ala Glu Arg Ala Ala Asp Leu Ile Lys Glu Ile
                565                 570
```

<210> SEQ ID NO 8
<211> LENGTH: 568
<212> TYPE: PRT
<213> ORGANISM: Aspergillus niger

<400> SEQUENCE: 8

```
Met Asp Ser Pro Ala His Tyr Asp Phe Val Ile Val Gly Gly Gly Thr
1               5                   10                  15

Ser Gly Leu Val Val Ala Asn Arg Leu Ser Glu Leu Ser Asp Val Thr
            20                  25                  30

Val Ala Val Ile Glu Ala Gly Glu Ser Ala Leu Asn Asn Phe Asn Val
        35                  40                  45

Ser Asn Val Met Gly Tyr Ser Thr Ala Phe Gly Thr Glu Val Asp Trp
50                  55                  60

Ala Tyr Gln Thr Glu Asn Gln Thr Tyr Ala Gly Leu Gln Gln Thr
65                  70                  75                  80

Ile Arg Ala Gly Lys Ala Leu Gly Gly Thr Ser Thr Ile Asn Gly Met
                85                  90                  95

Ser Tyr Thr Arg Ala Glu Asp Val Gln Ile Asp Asn Trp Glu Val Leu
            100                 105                 110

Gly Asn Asp Gly Trp Asn Trp Lys Asn Leu Phe Gln Tyr Tyr Lys Lys
            115                 120                 125

Ser Glu Gly Phe Gln Val Pro Thr Lys Asp Gln Ile Ala His Gly Ala
    130                 135                 140

Ser Tyr Asn Ala Ser Tyr His Gly Leu Asn Gly Pro Leu Lys Val Gly
145                 150                 155                 160

Trp Pro Asn Ser Met Thr Asn Ser Ser Val Phe Pro Val Leu Glu Gln
                165                 170                 175

Thr Phe Glu Lys Leu Gly Val Gln Tyr Asn Pro Asp Ser Gly Gly
            180                 185                 190

Lys Met Val Gly Phe Thr Val His Pro Asp Thr Leu Asp Arg Glu Met
    195                 200                 205

Asn Val Arg Glu Asp Ala Ala Arg Ala Tyr Tyr Trp Pro Tyr Glu Ala
    210                 215                 220

Arg Ser Asn Leu Lys Ile Ile Ser Asn Thr Arg Ala Asn Lys Val Ile
225                 230                 235                 240

Trp Ala Asn Thr Thr Gln Gly Glu Ala Val Ala Val Gly Ile Glu Val
                245                 250                 255

Thr Asn Ala Tyr Gly Thr Glu Thr Ile Tyr Ala Asp Lys Glu Val Ile
            260                 265                 270

Leu Ser Ala Gly Ala Leu Arg Ser Pro Ala Ile Leu Glu Leu Ser Gly
    275                 280                 285

Ile Gly Asn Pro Asp Val Leu Asn Lys His Asn Ile Pro Val Lys Val
    290                 295                 300

Asn Ile Thr Thr Val Gly Glu Asn Leu Gln Asp Gln Thr Asn Asn Ala
305                 310                 315                 320

Leu Ser Trp Glu Gly Val Asp Thr Leu Thr Gly Leu Ala Thr Phe Ser
                325                 330                 335

Val Leu Pro Ser Val Asn Gln Leu Tyr Gly Asp Asn Val Thr Ala Leu
            340                 345                 350

Ala Ser Tyr Val Lys Ser Gln Leu Ala Ser Tyr Ala Lys Thr Val Ala
        355                 360                 365

Ser Ala Ser Asn Gly Ala Val Lys Glu Ala Asn Leu Val Glu Ala Phe
    370                 375                 380

Glu Arg Gln Tyr Asp Leu Ile Phe Asn Ser Gln Val Pro Tyr Thr Glu
385                 390                 395                 400

Val Val Phe Ala Pro Ser Gly Asn Ser Phe Ala Val Glu Tyr Trp Pro
                405                 410                 415

Leu Leu Pro Phe Ser Arg Gly Ser Val His Ile Gln Ser Ala Asn Ala
```

```
                       420                 425                 430
Ser Asp Tyr Pro Ala Ile Asn Pro Asn Tyr Phe Met Phe Asp Gln Asp
            435                 440                 445

Ala Glu Ala Gln Val Thr Val Ala Gln Tyr Ile Arg Lys Ala Leu Gly
            450                 455                 460

Thr Ala Pro Leu Asn Ser Leu Val Gly Glu Val Ser Pro Gly Leu
465                 470                 475                 480

Asp Val Leu Pro Ala Ser Ala Ser Ser Ala Thr Trp Thr Lys Trp Val
                    485                 490                 495

Lys Glu Asn Tyr Arg Thr Asn Tyr His Pro Val Gly Thr Thr Ser Met
                500                 505                 510

Leu Pro Arg Glu Lys Gly Gly Val Val Ser Pro Glu Leu Lys Val Tyr
            515                 520                 525

Gly Thr Lys Asn Val Arg Val Val Asp Ala Ser Val Leu Pro Phe Gln
            530                 535                 540

Leu Cys Gly His Leu Thr Ser Thr Leu Tyr Ala Val Ala Glu Arg Ala
545                 550                 555                 560

Ser Asp Leu Ile Lys Glu Ser Tyr
                565

<210> SEQ ID NO 9
<211> LENGTH: 576
<212> TYPE: PRT
<213> ORGANISM: Aspergillus niger

<400> SEQUENCE: 9

Met Pro Ser Thr Arg Leu Cys Gly Pro Gln Tyr Asp Tyr Ile Val Val
1               5                   10                  15

Gly Gly Gly Thr Ser Gly Leu Val Val Ala Asn Arg Leu Ser Glu Asn
                20                  25                  30

Pro Asn Val Ser Val Leu Ile Ile Glu Ala Gly Gly Ser Val Leu Asn
            35                  40                  45

Asn Ser Asn Val Thr Asp Val Asn Gly Tyr Gly Leu Ala Phe Gly Thr
        50                  55                  60

Asp Ile Asp Trp Gln Tyr Glu Thr Ile Asn Gln Ser Tyr Ala Gly Asp
65                  70                  75                  80

Ala Pro Gln Val Leu Arg Ala Gly Lys Ala Leu Ser Gly Thr Ser Ala
                    85                  90                  95

Ile Asn Gly Met Ala Tyr Thr Arg Ala Glu Asp Val Gln Val Asp Ala
                100                 105                 110

Trp Gln Thr Ile Gly Asn Glu Gly Trp Thr Trp Asp Ser Leu Phe Pro
            115                 120                 125

Tyr Tyr Arg Lys Ser Glu Asn Leu Thr Ala Pro Thr Ala Ser Gln Arg
        130                 135                 140

Ala Arg Gly Ala Thr Tyr Asp Pro Ser Ala Asn Gly Glu Glu Gly Pro
145                 150                 155                 160

Leu Ser Val Ala Trp Pro Asp Ile Pro Ala Asn Asn Leu Thr Asn Thr
                165                 170                 175

Leu Asn Ala Thr Phe Gln Gly Leu Gly Val Pro Trp Thr Glu Asp Val
                180                 185                 190

Asn Gly Gly Lys Met Arg Gly Phe Asn Val Tyr Pro Ser Thr Ile Asp
            195                 200                 205

Tyr Thr Ala Tyr Val Arg Glu Asp Ala Ala Arg Ala Tyr Tyr Trp Pro
        210                 215                 220
```

```
Ile Ala Ser Arg Pro Asn Leu His Leu Met Leu Asp Thr Phe Val Asn
225                 230                 235                 240

Arg Leu Val Trp Lys Asn Gly Gly Ser Gln Gly Asn Ala Thr Ala Ala
                245                 250                 255

Gly Val Glu Ile Thr Ser Ser Asn Gly Thr Ile Ser Val Ile Gly Ala
            260                 265                 270

Ser Gln Glu Val Ile Ile Ser Ala Gly Ser Leu Lys Ser Pro Gly Ile
        275                 280                 285

Leu Glu Leu Ser Gly Ile Gly Asn Arg Asp Ile Leu Glu Arg Tyr Asn
    290                 295                 300

Ile Ser Val Arg Val Asp Leu Pro Thr Val Gly Glu Asn Leu Gln Asp
305                 310                 315                 320

Gln Thr Asn Ala Gly Leu Gly Ala Ser Thr Thr Pro Gly Leu Thr Gly
                325                 330                 335

Thr Lys Thr Val Val Tyr Pro Asn Val Tyr Asp Val Phe Gly Asn Asp
            340                 345                 350

Thr Leu Ala Val Ala Gln Ser Val Arg Arg Gln Leu Lys Gln Trp Ala
        355                 360                 365

Asn Glu Thr Ala Gln Val Ser Ser Gly Thr Met Lys Ala Glu Asp Leu
370                 375                 380

Glu Ala Leu Phe Gln Leu Gln Tyr Asp Leu Ile Phe Lys Asp Lys Ile
385                 390                 395                 400

Thr Ile Ala Glu Ile Leu Tyr Tyr Pro Gly Ser Thr Ser Ser Ile Ser
                405                 410                 415

Ala Gln Tyr Trp Ala Leu Met Pro Phe Ala Arg Gly His Val His Ile
            420                 425                 430

Ala Ser Ala Asp Pro Thr Ala Lys Pro Val Ile Asn Pro Asn Tyr Tyr
        435                 440                 445

Lys Phe Asp Trp Asp Leu Thr Ser Gln Ile Ala Val Ala Lys Tyr Val
    450                 455                 460

Arg Lys Thr Phe Gln Ser Ala Pro Leu Ala Asn Ile Ile Ala Glu Glu
465                 470                 475                 480

Thr Asn Pro Gly Phe Glu Ala Val Ala Ala Asn Gly Ser Glu Glu Asp
                485                 490                 495

Trp Lys Ala Trp Leu Leu Thr Gln Tyr Arg Ser Asn Phe His Pro Val
            500                 505                 510

Gly Thr Ala Ala Met Met Pro Gln Asp Lys Gly Gly Val Val Asn Asp
        515                 520                 525

Arg Leu Thr Val Tyr Gly Thr Ser Asn Val Arg Val Val Asp Ala Ser
    530                 535                 540

Val Leu Pro Phe Gln Val Cys Gly His Leu Val Ser Thr Leu Tyr Ala
545                 550                 555                 560

Val Ala Glu Arg Ala Ser Asp Leu Ile Lys Ala Asp Ser Ala Leu Phe
                565                 570                 575
```

US 8,999,691 B2

GLUCOSE DEHYDROGENASE

RELATED APPLICATIONS

This application claims priority from Japanese Patent Application No. 2010-147799 (filed on Jun. 29, 2010), the contents of which are incorporated herein by reference.

TECHNICAL FIELD

The present invention relates to glucose dehydrogenase associated with flavin adenine dinucleotide as a coenzyme (FAD-GDH), as well as to the production of the glucose dehydrogenase, and the use of the same for the quantitative determination of glucose.

BACKGROUND ART

The glucose concentration in blood is an important marker of diabetes. Enzymatic methods which use, for example, glucose oxidase (GOD), glucose-6-phosphate dehydrogenase (G6PDH), and glucose dehydrogenase associated with pyrroloquinoline quinone as a coenzyme (PQQGDH) have been used to measure glucose concentration. Since GOD requires oxygen as an electron acceptor, however, this technique has the drawback where the level of dissolved oxygen in the analyte influences the observed data. In case of G6PDH, the coenzyme NAD(P) must be added to the reaction, which will make the detection system complicated. PQQGDH has a high glucose oxidizing activity and thus offers an advantage in that oxygen is not required as an electron acceptor. However, it has a low selectivity for glucose and exhibits a certain activity with respect to maltose as well. Accordingly, there is a need for novel enzymes which can be used as a recognition element in glucose sensors. Moreover, to enable accurate measurement of the blood sugar level in patients who is receiving xylose absorption test, it is desirable that the enzyme have a low reactivity to xylose.

It has long been known that fungi have glucose dehydrogenase (see, for example, *Biochim. Biophys. Acta* 139(2), p. 265-276 (1967)). The following patent documents disclose glucose dehydrogenases from *Aspergillus* sp. and *Penicillium* sp., and the measurement of glucose concentration using such glucose dehydrogenases: Japanese Patent Application Laid-open Nos. 2007-289148, 2008-178380, 2008-035748 and 2008-035747, and WO 2007/11610, WO 2004/058958, WO 2006/101239 and WO 2007/139013. However, most enzymes of fungal origin are glycoproteins, which require glycosylation for functional expression. Because most of the extracellularly secreted enzymes such as glucose oxidase are highly glycosylated, it has been exceedingly difficult to produce such fungal glycoproteins by genetic recombinant techniques in *Escherichia coli*. Glucose dehydrogenases of fungal origin are also extracellularly secreted glycoproteins, and thus expression of recombinant fungal glucose dehydrogenases in *E. coli* is difficult. Even if the enzyme is expressed in *E. coli*, the productivity is low, thus the yield of enzyme per unit volume of culture is extremely low.

Patent Document 1: Japanese Patent Application Laid-open No. 2007-289148
Patent Document 2: Japanese Patent Application Laid-open No. 2008-178380
Patent Document 3: Japanese Patent Application Laid-open No. 2008-035748
Patent Document 4: Japanese Patent Application Laid-open No. 2008-035747
Patent Document 5: WO 2007/11610
Patent Document 6: WO 2004/058958
Patent Document 7: WO 2006/101239
Patent Document 8: WO 2007/139013
Non-Patent Document 1: Rolke et al., *Mol. Plant. Pathol.* 5(1), p. 17-27 (2004)

DISCLOSURE OF THE INVENTION

An object of the present invention is to provide a novel enzyme having a higher productivity and/or a higher thermal stability than conventional glucose dehydrogenases.

The inventor has isolated a gene coding for a novel FAD-GDH from *Botryotinia fuckeliana* and has discovered that, the productivity of recombinant expression in *E. coli* increases dramatically by replacing specific amino acid residues. The inventor has also discovered that, the thermal stability of the enzyme increases dramatically by replacing specific amino acid residues on flavin adenine dinucleotide glucose dehydrogenase (FAD-GDH) of fungal origin.

The invention provides a protein comprising the amino acid sequence set forth in SEQ ID NO:2, or a protein in which one or more amino acid residues are deleted, substituted or inserted in the amino acid sequence of SEQ ID NO:2 and having a glucose dehydrogenase activity, wherein the protein has the amino acid mutation selected from the group consisting of N176K, N176R, N176E, N176S, N225K, N225E, N259K, N301K, N326K, N326E, N330K, N330S, N355K, N355E, S514G and S552C, and a combination thereof. Preferably, the protein of the invention additionally comprises one or more mutations selected from the group consisting of G53A, E166R, T168P, N487S, S490P, N492T, A496E, D500E, V502L and A505N. More preferably, the protein of the invention comprises the amino acid sequence set forth in SEQ ID NO:2, wherein the protein has amino acid mutations selected from the group consisting of N176K/S490P/D500E/S514G/S552C, N176K/A496E/D500E/S514G/S552C, N176K/S514G/S552C, S514G/S552C and G53A/S514G/S552C. Even more preferably, the protein of the invention comprises the amino acid sequence set forth in SEQ ID NO:2, wherein the protein has amino acid mutations selected from the group consisting of N176K/N301K/N330K/S514G/S552C, N176R/N301K/N330K/S514G/S552C, N176R/N225E/N301K/N326E/N330K/N355E/55140/S5520, N176K/S490P/D500E/S514G/S552C and E166R/T168P/N176R/N301K/N330K/S490P/D500E/S514G/5552C.

In another aspect, the invention provides a protein comprising the amino acid sequence set forth in SEQ ID NO:4, or a protein in which one or more amino acid residues are deleted, substituted or inserted in the amino acid sequence of SEQ ID NO:4 and having a glucose dehydrogenase activity, wherein the protein has the amino acid mutations V149C and G190C.

In still another aspect, the invention provides a glucose dehydrogenase of fungal origin, wherein both amino acids at the positions that correspond to V149 and G190 when an amino acid sequence thereof is aligned with the amino acid sequence set forth in SEQ ID NO:4 are substituted with cysteine. Preferably, the glucose dehydrogenase of fungal origin of the invention is characterized by having an amino acid sequence selected from the group consisting of SEQ ID NO:2 and SEQ ID NOs: 5 to 9, wherein both amino acids at the positions corresponding to V149 and G190 on the amino acid sequence of SEQ ID NO:4 are substituted with cysteine.

In yet another aspect, the invention provides a protein comprising the amino acid sequence set forth in SEQ ID NO: 2, or a protein in which one or more amino acid residues are deleted, substituted or inserted in the amino acid sequence set forth in SEQ ID NO: 2 and having a glucose dehydrogenase activity, wherein the protein has the amino acid mutations A150C/T192C.

In further aspect, the invention provides a gene encoding the glucose dehydrogenase of the present invention, a recombinant vector comprising such a gene, and a transformant or transductant obtained by transformation with such a recombinant vector. The invention also provides a method of producing glucose dehydrogenase comprising culturing the transformant obtained by transformation, with the recombinant vector comprising the gene encoding the glucose dehydrogenase of the invention, and collecting glucose dehydrogenase from the culture.

In a still further aspect, the invention provides a method of analyzing glucose comprising measuring the concentration of glucose in a sample using the glucose dehydrogenase of the invention. The invention further provides a glucose assay kit comprising the glucose dehydrogenase of the invention. The invention still further provides an enzyme electrode comprising the glucose dehydrogenase of the invention immobilized on a surface of the electrode, and a glucose sensor comprising the enzyme electrode of the invention as a working electrode.

In yet another aspect, the invention provides a biosensor for measuring glucose, which comprises a protein having the amino acid sequence set forth in SEQ ID NO:2, or a protein in which one or more amino acid residues are deleted, substituted or inserted in the amino acid sequence of SEQ ID NO:2, wherein the protein exhibits no glucose oxidase activity, and has a glucose dehydrogenase activity, and wherein the protein has a reactivity to xylose not higher than 20% of the reactivity to glucose, and the reactivity is not influenced by dissolved oxygen.

BRIEF DESCRIPTION OF THE DRAWINGS

FIG. 1-1 shows an alignment of the amino acid sequences of glucose dehydrogenases of fungal origin. In the diagram, the amino acid residue V at the position 149 and the amino acid residue G at the position 190 on FAD-GDH from *Aspergillus oryzae* T1, and amino acid residues corresponding to these amino acid residues, are shown in bold. The symbols have the following meanings.
Aspcal__10864: *Aspergillus carbonarius* ITEM 5010; GenBank Aspcal__10864
Aspcal__33771: *Aspergillus carbonarius* ITEM 5010; GenBank Aspcal__33771
Bfu (Aj__555871): Botryothinia fuckeliana (GenBank AJ 555871)
Ssc (XP__001584680): Sclenotinia sclerotiorum (GenBank XP__001584680)
40715 (XP 001394544): *Aspergillus niger* 40715 (GenBank XP__001394544)
39269 (XP__001391138): *Aspergillus niger* 39269 (GenBank XP__001391138)
AoT1 FADGDH: *Aspergillus oryzae* T1 FAD-GDH.
FIG. 1-2 shows an alignment of the amino acid sequences of glucose dehydrogenases of fungal origin.
FIG. 1-3 shows an alignment of the amino acid sequences of glucose dehydrogenases of fungal origin.
FIG. 2 shows cultivation curves for *E. coli* transformants comprising a recombinant FAD-GDH gene from *Botryotinia fuckeliana*.
FIG. 3 shows the thermal stability of wild-type and modified FAD-GDH from *Aspergillus oryzae*.

PREFERRED EMBODIMENTS OF THE INVENTION

Figure 2:
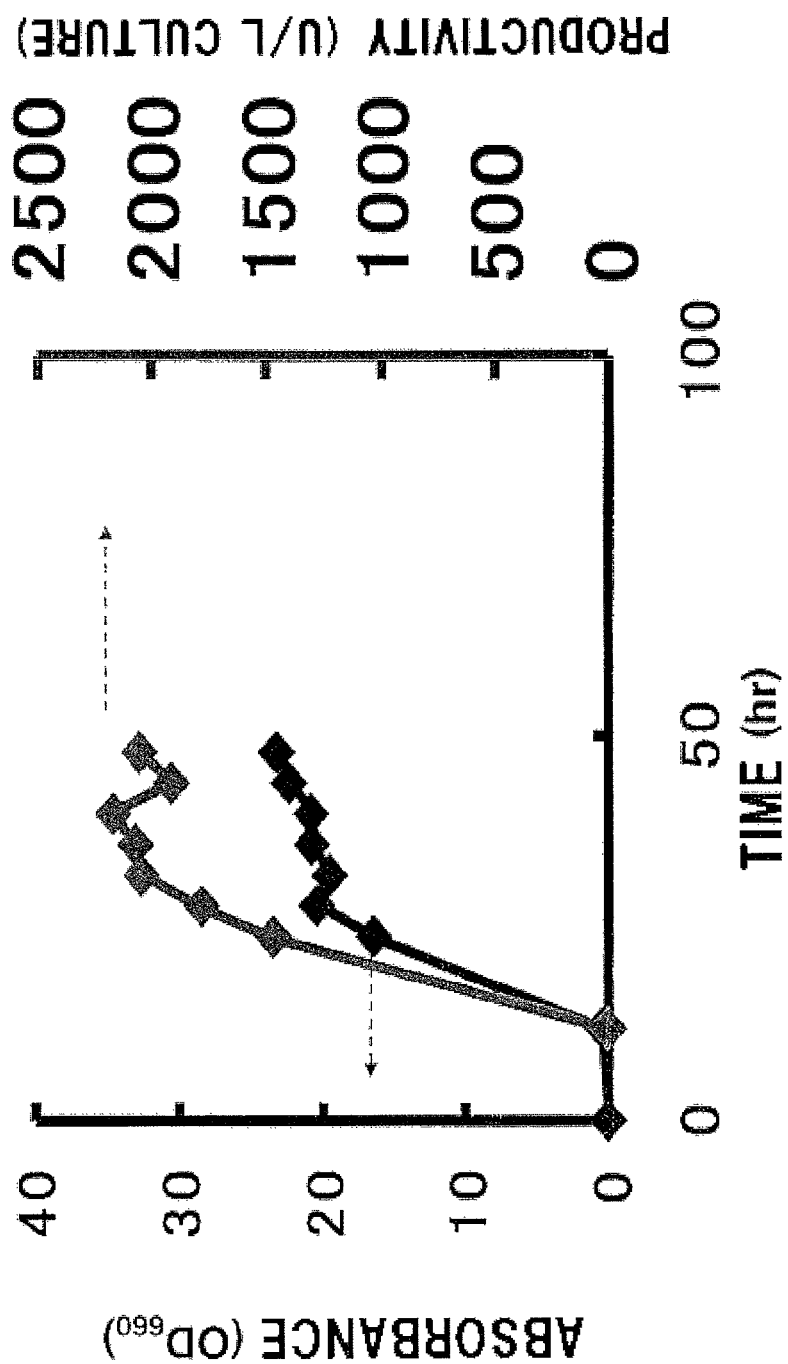

FAD-GDH from *Botryotinia fuckeliana*
In the present invention, the FAD-GDH in *Botryotinia fuckeliana* was identified. The amino acid sequence is shown in SEQ ID NO:1. Although the genome sequence for *Botryotinia fuckeliana* has been publicly disclosed, there have hitherto been no reports indicating that *Botryotinia fuckeliana* has FAD-GDH. No genes have been annotated for FAD-GDH. The protein having the amino acid sequence shown in SEQ ID NO:1 had been inferred to be glucose oxidase (GOD) (Rolke et al., *Mol. Plant. Pathol.* 5(1), p. 17-27 (2004)). The present inventor has shown for the first time that this protein is in fact not GOD but rather GDH. Contrary to GOD, GDH is not influenced by dissolved oxygen upon glucose measurement, and thus is useful as a recognition element in biosensors for measuring glucose. The amino acid sequence shown in SEQ ID NO:1 has a sequence homology of about 30 to 60% with the amino acid sequences of known glucose dehydrogenases of fungal origin. For example, it has an amino acid homology of about 57% with glucose dehydrogenase from *Aspergillus oryzae* T1 (GenBank ACW04779.1).

In the present invention, to improve the productivity of the recombinant expression in *E. coli*, the putative signal sequence was removed to obtain the amino acid sequence of SEQ ID NO:2. Namely, the sequence from the N-terminus to the serine residue (Ser) at the position 17 on the native FAD-GDH from *Botryotinia fuckeliana* shown in SEQ ID NO:1 was removed and a methionine residue (Met) was added to the N-terminal.

Modified FAD-GDH from *Botryotinia fuckeliana*
The inventor has discovered that modified FAD-GDH having the single mutation N176K, S514G or S552C, the double mutation S514G/S552C or the triple mutation N176K/S514G/S552C in the amino acid sequence of SEQ ID NO:2 exhibit a higher productivity in *E. coli* than wild-type FAD-GDH, and that modified FAD-GDH having the triple mutation N176K/S514G/S552C exhibits both a high productivity and a high enzyme activity.

As used herein, the positions of amino acid mutations in the amino acid sequence of FAD-GDH from *Botryotinia fuckeliana* are numbered, with the first residue methionine on the amino acid sequence of SEQ ID NO:2 being labeled as "1." Also, as used herein, amino acid mutations or substitutions are denoted by indicating in order the original amino acid residue, the position of the amino acid, and the amino acid residue following substitution. For example, "S514G" indicates that the S residue at the position 514 is replaced with G residue. Combinations of two or more mutations are indicated with a slash (/).

As used herein, the phrase "an enzyme having a high productivity in *E. coli*" means that the enzyme recombinantly expressed in the host *E. coli* and isolated from the culture has a high enzyme activity per unit volume of the culture solution (U/L). At a high productivity, the enzyme can be recombinantly produced with a smaller culturing apparatus and at a lower cost. The amino acid sequence of the enzyme is responsible for the differences in, for example, the water solubility of the protein, the folding efficiency, the enzyme activity per unit protein and the stability of the enzyme, which collectively reflect the enzyme productivity. In addition, the amino acid sequence of the enzyme would also affect other characteristics, for example, the rate of recombinant expression in the host per unit volume of culture solution, tendency to form inclusion bodies, and the stability of the enzyme within the bacterial cells and in the purification process.

Moreover, it is preferable for the modified FAD-GDH from *Botryotinia fuckeliana* to have a multiple mutation comprising the mutation N176K, N176R, N176E, N176S, N225K, N225E, N259K, N301K, N326K, N326E, N330K, N330S, N355K, N355E, S514G or S552C in combination with one or more mutations selected from the group consisting of G53A, E166R, T168P, N487S, S490P, N492T, A496E, D500E, V502L and A505N. Of these multiple mutation enzymes, preferred examples are N176K/S490P/D500E/S514G/S552C, G53A/N176K/S490P/D500E/S514G/S552C, N176K/A496E/D500E/S514G/S552C, N176K/A496E/D500E/V502L/S514G/S552C, G53A/N176K/A496E/D500E/V502L/S514G/552C, N176K/S514G/S552C, S514G/S552C and G53A/S514G/S552C. More preferred examples are N176K/S490P/D500E/S514G/S552C, N176K/A496E/D500E/S514G/S552C, N176K/S514G/S552C, S514G/S552C and G53A/S514G/S552C. Particularly preferred examples are
N176K/N301K/N330K/S514G/S552C, N176R/N301K/N330K/S514G/S552C, N176R/N225E/N301K/N326E/N330K/N355E/S5140/S552C, N176K/S490P/D500E/S514G/S552C and E166R/T168P/N176R/N301K/N330K/S490P/D500E/S5140/S552C.

In addition, these modified FAD-GDHs from *Botryotinia fuckeliana* have higher glucose selectivities relative to xylose than does FAD-GDH from *Aspergillus oryzae* Ti.

Modified FAD-GHD of Improved Thermal Stability

The inventor has discovered that the thermal stability increases dramatically compared with the wild-type FAD-GDH by substituting both the amino acid residue V at the position 149 and the amino acid residue G at the position 190 on the *Aspergillus oryzae* T1-derived FAD-GDH shown in SEQ ID NO:4 with cysteines (C). The amino acid sequence of *Aspergillus oryzae* T1-derived GAD-GDH is shown in SEQ ID NO:3. In the present invention, to improve the productivity of the recombinant expression in *E. coli*, the putative signal sequence was removed to obtain the amino acid sequence of SEQ ID NO:4. Namely, the sequence from the N-terminus to the lysine (Lys) residue at the position 23 on the native FAD-GDH from *Aspergillus oryzae* shown in SEQ ID NO:3 was removed and a methionine residue (Met) was added to the N-terminal. As used herein, the positions of amino acid mutations on the amino acid sequence of FAD-GDH from *Aspergillus oryzae* are numbered with the first residue methionine on the amino acid sequence of SEQ ID NO:4 being labeled as "1."

As used herein, "thermally stable" means that, when an enzyme is incubated for a given length of time at a high temperature (e.g., 45° C., 50° C., 55° C., or 60° C.) and the enzyme activity is measured, the decrease in enzyme activity over time is limited. The thermal stability may, for example, be expressed as the residual activity after the enzyme is incubated for a give length of time at a given temperature, or may be expressed as the inactivation constant and/or the half-life of the enzyme activity determined from the slope of the curve (inactivation curve) obtained from a plot of enzyme activity versus incubation time.

In addition to the mutations in the amino acid residues at the positions 149 and 190 on SEQ ID NO:4, the modified FAD-GDH of the invention may also have other mutations, as long as it has a glucose dehydrogenase activity. One or more, for example from one to ten, amino acid residues on SEQ ID NO:4 may be replaced with any other amino acid residues.

The inventor has also discovered that the thermal stability of FAD-GDH from *Botryotinia fuckeliana* or other fungi similarly increases when both the amino acid residues corresponding to the amino acid residues at the positions 149 and 190 on the *Aspergillus oryzae* T1-derived FAD-GDH are replaced with cysteine.

Alignments of the amino acid sequences for several FAD-GDHs of fungal origin are shown in FIG. 1. The sequences shown in the figure were obtained by removing the region assumed to be the N-terminal signal peptide from the amino acid sequence of each enzyme, and adding methionine at the N-terminus. The amino acid residues corresponding to the amino acid residue V at the position 149 and the amino acid residue G at the position 190 on FAD-GDH from *Aspergillus oryzae* T1 are shown in bold. In the present invention, the genes coding for the amino acid sequences of the enzymes were totally synthesized, then recombinantly expressed in *E. coli*. The enzymes thus obtained were confirmed to have the GDH activity. Moreover, as shown in Example 8 below, the thermal stability was improved by replacing both of the amino acid residues corresponding to the amino acid residue V at the position 149 and the amino acid residue G at the position 190 on the *Aspergillus oryzae* T1-derived FAD-GDH with C residues. Among these modified FAD-GDHs, some showed a decline in enzyme activity compared with the wild-type enzyme. However, because the thermal stability increases, inactivation during purification and storage of the enzyme decreases, which is beneficial from the standpoint of productivity on an industrial scale. Moreover, it is also possible to develop modified FAD-GDHs having a high productivity on an industrial scale by combining other mutations which increase the enzyme activity and productivity in *E. coli*.

It will be apparent to persons skilled in the art that, by aligning the amino acid sequences in accordance with conventional practice for FAD-GDHs from fungi other than the fungi illustrated in FIG. 1, the amino acid residues at positions which correspond to the amino acid residue V at the position 149 and the amino acid residue G at the position 190 on the FAD-GDH from *Aspergillus oryzae* T1 can be determined, and that FAD-GDHs of improved thermal stability can be obtained by replacing these residues with C residues. As used herein, the expression "amino acid residue at a position corresponding to - - - " refers to the amino acid residue present at a position corresponding to a specific amino acid residue on the reference protein when the amino acid sequence of a target protein is aligned with the amino acid sequence of the reference protein. The alignment may be created using any of the numerous software known in the art. For example, use may be made of the software AlignX (Invitrogen; Lu, G., and Moriyama, E. N.: "Vector NTI, a balanced all-in-one sequence analysis suite," *Brief Bioinform.* 5, 378-88 (2004)) available from Vector NTI, with the default parameters.

Method of Preparing FAD-GDH

The FAD-GDH of the invention may be produced by recombinant expression using a technique commonly known in the art. The sequences of the genes coding for native FAD-GDH from *Botryotinia fuckeliana* and FAD-GDH from *Aspergillus oryzae* T1 can each be easily determined based on the amino acid sequences shown in SEQ ID NO:2 and SEQ ID NO:4, respectively. The gene coding for a FAD-GDH may be cloned from the genome of *Botryotinia fuckeliana* or *Aspergillus oryzae*, or prepared by PCR using a series of chemically synthesized oligonucleotides, or totally synthesized using, for example, an automated DNA sequencer. It is desirable to suitably design or modify the nucleotide sequence by selecting codons so as to achieve a high level of expression in the host organism to be used. The characteristics of codon usage in specific host organisms are well known in the art.

The gene coding for the modified FAD-GDH of the invention may be constructed from the gene coding for the native FAD-GDH by replacing the nucleotide sequence which encode the amino acid residues to be substituted with a nucleotide sequence which encode the desired amino acid residues. Various methods for such site-specific mutation are well known in the art, such as PCR using suitably designed primers. Alternatively, a gene coding for a modified amino acid sequence may be totally synthesized.

So long as the FAD-GDH of the invention has the desired glucose dehydrogenase activity, one or more other amino acid residue therein may also be deleted or substituted, or other amino acid residues may be added. Moreover, it is desirable for such modified FAD-GDHs to have a sequence homology of at least 80% with the native FAD-GDH. The sequence homology is preferably at least 85%, more preferably at least 90%, and even more preferably at least 95%.

The gene thus obtained is inserted in an expression vector, which is then used to transform a suitable host (e.g., *E. coli*). Many host-vector systems for the expression of exogeneous proteins are known in the art. Various bacteria, yeasts, cultured cells and the like can be used as the host. In cases where the production of a glycosylated glucose dehydrogenase is desired, eukaryotic cells are used as the host. The resulting transformant is cultured in accordance with conventional practice, and FAD-GDH can be recovered from the cells or the culture.

In one preferred embodiment of the invention, the *E. coli* transformant is cultured in the medium referred to as "ZYP broth" in F. William Studier et al. (2005) Protein Expression and Purification (herein referred to as "Medium A"). This medium is prepared from LB medium commonly used as an *E. coli* medium, supplemented with 0.5% glycerol, 0.05% glucose, 0.2% α-lactose, 25 mM of $(NH_4)_2SO_4$, 100 mM of $KH_2PO_4$, 100 mM of $NaHPO_4$ and 1 mM of $MgSO_4$.

The recombinant protein is expressed by culturing the transformant in Medium A at between 15° C. and 25° C., and preferably about 20° C. In this way, a higher productivity may be achieved compared with the conventional IPTG induction procedure. In addition, by co-expressing the modified enzyme of the invention with the chaperones GroEL and GroES, which are known to promote protein folding, even higher productivity can be obtained. Co-expression with chaperones may be carried out by introducing an expression vector containing a gene coding for the modified enzyme of the invention into *E. coli* together with a vector which expresses the GroEL and GroES genes under arabinose induction (e.g., the commercially available chaperone vector pGro7, from TaKaRa). After the transformant has grown to some degree, arabinose is added to induce chaperone expression.

The recombinant FAD-GDH thus obtained can be purified using any purification techniques known in the art, such as gel filtration, ion-exchange chromatography, affinity chromatography, liquid chromatography, filtration, ultrafiltration, salting out, solvent precipitation, immunoprecipitation, gel electrophoresis, isoelectric focusing and dialysis.

Method of Measuring Enzyme Activity

The FAD-GDH of the invention catalyzes the oxidation of glucose to produce gluconolactone with FAD serving as a coenzyme. The glucose dehydrogenase activity of the FAD-GDH of the invention can be determined by a colorimetric reaction that employs a redox dye to quantitatively measure the amount of FAD which is reduced in association with glucose oxidation by dehydrogenase. The colorimetric reagent may include, for example, phenazine methosulfate (PMS), 2,6-dichlorophenol indophenol (DCIP), potassium ferricyanide or ferrocene. The glucose oxidation activity of FAD-CDH may be measured by quantitatively determining the hydrogen peroxide that forms from the reaction of the dehydrogenase with the substrate. Hydrogen peroxide may be measured by using, for example, peroxidase and Trinder's reagent (TODB) or 4-aminoantipyrine to monitor the change in the absorbance of the dye.

Selectivity for Glucose

The selectivity for glucose of the FAD-GDH of the invention can be evaluated by measuring the enzyme activity in the manner described above using various types of sugars as the substrate, such as mannose, galactose, xylose, lactose and maltose, and determining the relative activity with respect to the activity when glucose is used as the substrate.

The FAD-GDH of the invention has a high selectivity for glucose. In particular, the reactivities of the FAD-GDH with maltose and galactose were equal to or below the measuring limit. Accordingly, assay kits or enzyme sensors created using the FAD-GDH of the invention have a high selectivity for glucose measurement, and thus possess the advantage of assaying glucose at a high sensitivity even when other sugars such as maltose are present or possibly present in the specimens to be tested.

Another feature of the FAD-GDH of the invention is that it has a low reactivity to xylose, which is advantageous in that even when a xylose absorption test is carried out for the patient, the blood sugar level can be accurately measured.

Glucose Assay Kit

The present invention also provides a glucose assay kit comprising the FAD-GDH according to the invention. The glucose assay kit of the invention comprises the FAD-GDH according to the invention in a sufficient amount for at least one assay. In addition to the FAD-GDH of the invention, the kit typically comprises a buffer solution required for the assay, a mediator, a glucose standard solution for preparing a calibration curve, and guidelines for use. The FAD-GDH according to the invention can be provided in various forms, such as a freeze-dried reagent or as a solution within a suitable storage solution.

Glucose Sensor

The present invention further provides an enzyme electrode where the FAD-GDH according to the invention has been immobilized on the surface, as well as a glucose sensor comprising such an enzyme electrode. A carbon electrode, gold electrode, platinum electrode or the like is used as the electrode, and the enzyme of the invention is immobilized on the electrode. Carbon electrodes may include electrodes produced by screen printing. Gold or platinum electrodes may include those produced by sputtering. Methods of immobilization may include, for example, the use of a crosslinking reagent, encapsulation within a polymer matrix, coating with a dialysis membrane, and the use of a photo-crosslinkable polymer, a conductive polymer or a redox polymer. Also the enzyme may be immobilized in a polymer or adsorbed to the electrode together with ferrocene or a derivative thereof as the electron mediator. Combinations of these methods may also be used. Typically, the FAD-GDH of the invention is immobilized on a carbon electrode using glutaraldehyde, followed by treatment with a reagent having an amine group to block the free aldehyde groups.

Measurement of glucose concentration may be carried out as follows. A buffer solution is placed in a constant-temperature cell, the mediator is added, and the temperature is held constant. Potassium ferricyanide, phenazine methosulfate, a ruthenium complex or the like may be used as the mediator. An electrode on which the FAD-GDH of the invention has been immobilized is used as the working electrode. Also a counterelectrode (e.g., a platinum electrode) and, if necessary, a reference electrode (e.g., an Ag/AgCl electrode) are used. A given voltage is applied to the carbon electrode and, once the current achieves a steady state, a glucose-containing sample is added and the increase in current is measured. The glucose concentration within the specimen can be calculated in accordance with the calibration curve prepared with standard glucose solutions of predetermined concentration.

The FAD-GDH of the invention is especially useful in devices for assaying the blood sugar level. The assay device may have a construction similar to that of the commercially available amperometric biosensor test strips for measuring blood sugar level. By way of illustration, the assay device may have two electrodes (a working electrode and a reference electrode) mounted on an insulator, a reagent port and a sample receiver. The FAD-GDH of the invention and the mediator are placed in the reagent port. When a blood sample, for instance, is added to the sample receiver, the glucose in the sample reacts with the FAD-GDH, generating a current. The glucose concentration (blood sugar level) can be determined from the current. In addition to electrochemical detection, glucose can also be measured using an optical sensor.

As used herein, embodiments expressed with the term "comprising" should understood as encompassing both embodiments expressed with the term "essentially consisting of" and embodiments expressed with the term "consisting of."

The contents of all patents and reference documents explicitly cited in the description are incorporated herein by reference in their entirety.

The invention is described in more detail below by way of examples, although these examples are not intended to limit the scope of the invention.

EXAMPLES

The invention is described in more detail below by way of examples, although the invention is not limited by these examples.

Example 1

Preparation of Recombinant Genes of Glucose Dehydrogenase from *Botryotinia fuckeliana* (Bfu-GDH) and Glucose Dehydrogenase from *Aspergillus oryzae* (Ao-GDH)

The amino acid sequence of glucose dehydrogenase from *Botryotinia fuckeliana* is shown in SEQ ID NO:1. The region from the N-terminus to Ser at the position 17 is assumed to be the signal peptide. For example, the free access server SignalP 3.0 Server (http://www.cbs.dtu.dk/services/SignalP-3.0/) can be used for predicting the signal sequence cleavage site. This server is operated by The Center for Biological Sequence analysis at the Technical University of Denmark, and conducts a search for potential signal sequences in a given amino acid sequence, and predicts the cleavage sites for the sequences based on the methodology described in the following report: "Identification of prokaryotic and eukaryotic signal peptides and prediction of their cleavage sites," by Henrik Nielsen, Jacob Engelbrecht, Soren Brunak and Gunnar von Heijne, in *Protein Engineering*, 10:1-6 (1997). According to a prediction obtained using the SignalP 3.0 Server, the region from the N-terminus to the Ser residue at the position 17 was predicted to be a signal peptide sequence. Thus a nucleotide sequence which encodes the amino acid sequence having the initiation methionine and downstream sequence from the Thr residue at the position 18 was designed with a codon usage suitable for recombinant production by *E. coli* and totally synthesized. The amino acid sequence of the protein (referred to below as "Bfu-GDH") encoded by the gene thus obtained is shown in SEQ ID NO:2.

The amino acid sequence of the glucose dehydrogenase from *Aspergillus oryzae* T1 is shown in SEQ ID NO:3. According to a prediction from the SignalP 3.0 Server, the region from the N-terminus to the Lys residue at the position 23 was predicted to be a signal peptide. A nucleotide sequence which encodes the amino acid sequence having the initiation methionine and the downstream sequence from the Asn residue at the position 24 was designed and totally synthesized. The amino acid sequence of the protein (referred to below as "Ao-GDH") encoded by the gene thus obtained is shown in SEQ ID NO:4. *E. coli* BL21(DE3) (F—, ompT, hsdSB(rB- mB-), gal(λcI 857, ind1, Sam7, nin5, LacUV5-T7gene1), dcm(DE3): from Novagen) was used as the host for recombinant production. The gene expression vector used was pET30c (kan, LacI; from Novagen), and the chaperone co-expression vector used was pGro7 (GroEL, GroES; from TaKaRa).

Example 2

Measurement of Enzyme Activity

Measurement of the glucose dehydrogenase activity of the FAD-GDH of the invention was carried out by quantitatively measuring the change over time in absorbance at 600 nm, which indicates the color fading of 2,2'-dichlorodiisopropyl ether (DCIP) reduced by the reaction of the dehydrogenase with the substrate. Unless noted otherwise, the reaction was carried out under the following conditions. The reaction was initiated by adding substrate to the reaction solution containing the enzyme (10 mM potassium phosphate (pH 7.0)+0.6 mM PMS+0.06 mM DCIP; the concentrations are indicated as final concentrations), and the change in absorbance at 600 nm was monitored. Glucose having a final concentration of 50 mM was used as the substrate, and the amount of enzyme which reduces 1 μmol of DCIP was defined as 1 unit. The activity was calculated with the following formula. The molar absorption coefficient of DCIP at pH 7.0 was set to 16.3 $mM^{-1}$ $cm^{-1}$.

unit/mL=ΔABS/min×1/16.3×10

The glucose oxidation activity of the FAD-GDH of the invention was determined by measuring hydrogen peroxide generated by the reaction of dehydrogenase with the substrate in the presence of peroxidase, Trinder's reagent (TODB) and 4-aminoantipyrine. The change over time in the absorbance at 546 nm was monitored. Unless noted otherwise, the reaction was carried out under the following conditions. The reaction was initiated by adding the substrate to the reaction solution containing the enzyme (10 mM potassium phosphate (pH 7.0)+1.5 mM 4-aminoantipyrine+1.5 mM TODB+2 U/mL peroxidase; concentrations are indicated as final concentrations), and the change in absorbance at 546 nm was monitored. Glucose having a final concentration of 50 mM was used as the substrate, and the amount of enzyme which generates 1 μmol of hydrogen peroxide per minute was defined as 1 unit. The molar absorption coefficient of TODB at pH 7 was set to 38 $mM^{-1}cm^{-1}$. The activity was calculated from the change in the absorption with the formula.

unit/mL=ΔABS/min×2/38×10 unit/mg=Unit/mL/mg of protein/mL

Example 3

Investigation of Culturing Conditions, and Production of Partially Purified Enzyme Preparation 1. Production of Bfu-GDH Using IPTG Induction:

E. coli BL21(DE3) was transformed with the expression vector pET30c bearing the gene coding for Bfu-GDE. The resulting transformant, BL21(DE3)/pET30c(Bfu-GDH), was inoculated into 3 mL of LB medium and cultured with shaking at 37° C. overnight. Next, 1 mL of pre-culture solution was inoculated into 100 mL of LB medium (kanamycin (Km, 50 µg/mL) and cultured with shaking at 37° C. and 180 rpm using an Erlenmeyer flask with baffle. When the OD660 value for the culture solution approached 0.6, isopropyl-β-thiogalactopyranoside (IPTG; final concentration, 1 mM) was added to induce Bfu-GDH expression. Following addition, culturing was continued at 20° C. and stopped 14 hours from the start of culturing. During culturing, 300 µL of the culture medium was taken once every several hours, 60 µL of Bug-Buster Reagent was added to the collected cells, and the cells were lysed by shaking at 4° C. for 20 minutes. Next, 60 µL of 10 mM potassium phosphate was added and centrifuged (16,000×g, 4° C., 20 minutes). The supernatant was collected as a partially purified enzyme preparation, and the enzyme activity was measured. The enzyme activity increased as the cell concentration increased, and became 65 Upper liter of culture solution at the end of cultivation. At this time, the specific activity was 0.15 U/mg, and the cell concentration in terms of the OD660 value was 4.0.

2. Production of Bfu-GDH Using Medium A:

The production of Bfu-GDH using Medium A was carried out. E. coli BL21(DE3) was transformed with the expression vector pET30c bearing the gene coding for Bfu-GDH. The resulting transformant, BL21(DE3)/pET30c(Bfu-GDH), was inoculated into 3 mL of LB medium and cultured with shaking at 37° C. overnight. Next, 1 mL of pre-culture solution was inoculated into 100 mL of Medium A shown below (Km, 50 µg/mL) and cultured with shaking at 20° C. and 120 rpm using a Sakaguchi flask. Medium A: LB medium+0.5% glycerol, 0.05% glucose, 0.2% α-lactose, 25 mM of $(NH_4)_2SO_4$, 100 mM of $KH_2PO_4$, 100 mM of $NaHPO_4$, 1 mM of $MgSO_4$ (obtained by modifying the ZYP medium; F. William Studier et al., Protein Expression and Purification (2005)).

During culturing, 300 µL of the culture solution was collected at arbitrary time intervals, 60 µl of BugBuster Reagent was added to the collected cells, and the cells were lysed by shaking at 4° C. for 20 minutes. Next, 60 µL of 10 mM potassium phosphate was added and centrifuged (16,000×g, 4° C., 20 minutes). The supernatant was collected as a partially purified enzyme preparation and the enzyme activity was measured.

Bfu-GDH was expressed as a water-soluble enzyme having a GDH activity. The cultivation and enzyme production curves are shown in FIG. 2. The OD660 value underwent a large increase for 24 hours following the start of culturing. The increase stopped at a value of about 21 at about 28 hours. The enzyme activity increased from about 24 hours, reaching about 2,200 U per liter of culture solution after 32 hours, at which point the increase in the activity stopped. The protein concentration was 2.2 mg/mL after 24 hours, and was about 3.0 mg/mL after 36 hours, at which point increase in the concentration stopped.

As a result of measuring the enzyme activity of the partially purified preparation of the glucose dehydrogenase from Botryotinia fuckeliana (Bfu-GDH) obtained by cultivation in Medium A, only the glucose dehydrogenase activity was detected, but no glucose oxidase activity was observed. In previously published academic reports, the gene from Botryotinia fuckeliana has been reported to be a gene coding for glucose oxidase. The above results show for the first time that the protein encoded by this gene is in fact glucose dehydrogenase. A method for preparing a novel glucose dehydrogenase having a low reactivity to xylose is described in Example 4. At 40 hours following the start of culturing, the amount of cells increased and the enzyme productivity per unit protein becomes 1.8 U/mg of protein, which is 12 times that of the IPTG system. As a result, an enzyme production amount of 2,200 Upper liter of culture solution was achieved, which was 34 times that observed in the IPTG system. In other words, it was found that Bfu-GDH can be recombinantly produced more efficiently using Medium A than using the IPTG system.

3. Production of Bfu-GDH Using Medium A, and Co-Expression with Chaperones:

E. coli BL21(DE3)/pGro7 already containing the chaperone vector pGro7 was transformed with the expression vector pET30c bearing a Bfu-GDH codon repair gene. pGro7 is a vector that expresses the chaperones GroEL and GroES under arabinose induction, which are known to promote protein folding. The resulting transformant BL21(DE3)/pET30c (Bfu-GDH).gGro7 was inoculated into 3 mL of LB medium and cultured with shaking at 37° C. overnight. Next, 1 mL of pre-culture solution was inoculated into 100 mL of Medium A containing 50 µg/mL of Km and 50 µg/mL of chloramphenicol (Cm), and cultured with shaking at 20° C. and 120 rpm using a Sakaguchi flask. Arabinose was added (final concentration, 2 mM) to induce pGro7 expression. The timing of the arabinose addition was investigated by varying the time of addition: at the start of culturing, 12 hours after the start of culturing, and 24 hours after the start of culturing. During culturing, 300 µL of culture fluid was collected at arbitrary time intervals, and partially purified preparations were produced by the same method as described above.

Arabinose (final concentration, 2 mM) was added at the start of culturing, after 12 hours, and after 24 hours. In each of these cases, the OD660 value increased markedly from the start of culturing until 24 hours thereafter, and the increase in the OD660 values stopped after 32 hours, reaching the values of about 27, about 28 and about 26, respectively. In addition, the enzyme activity increased from about 24 hours, and the increase stopped after 40 hours at about 2,500 U/L, 2,600 U/L and 1,300 U/L, respectively. The protein concentrations after 24 hours were 1.8 mg/mL, 2.0 mg/mL and 1.9 mg/mL, respectively. When arabinose was added at the start of culturing, the increase in the protein concentration stopped 36 hours later at about 3.2 mg/mL. When arabinose was added 12 hours and 24 hours after the start of culturing, the protein concentration increased gradually until 48 hours after the start of culturing. These results indicate that the productivity of Bfu-GDH was enhanced by co-expression with chaperone.

Example 4

Evaluation of Substrate Specificity

The substrate specificity of the enzyme obtained with Medium A in Example 3 above was measured using glucose, maltose, xylose and galactose as the substrates. At a substrate concentration of 5 mM, dehydrogenase activity of Bfu-GDH (with the activity for glucose being 100%) was not detected for maltose and galactose, and the dehydrogenase activity was 13% for xylose. The xylose dehydrogenase activity of Ao-GDH under the same conditions (with the activity for glucose being 100%) was 21%. The results indicate that Bfu-GDH exhibited a lower enzyme activity with respect to xylose than the already reported activity of Ao-GDH.

Example 5

Introduction of Mutations into Bfu-GDH

Site-specific mutagenesis was carried out by the QuikChange™ method. In the QuikChange™ method, the pET30c-Bfu-GDH created in Example 1 was used as the template, and amplified by PCR with mutagenesis primers. Next, DpnI was added to the reaction mixture and incubated at 37° C. for 60 minutes to digest the template DNA, and *E. coli* DH5a was transformed. After culturing overnight in an LB agar culture (50 μg/mL kanamycin), the plasmid was extracted from randomly selected clones, and the sequence was analyzed to confirm that the target mutation was introduced. The resulting PCR products were NdeI and HindIII digested (37° C., 2 hours), ligated with the same restriction enzyme-digested pET30c, and *E. coli* BL21(DE3) was transformed. After culturing overnight In an LB agar medium (50 μg/mL kanamycin), the plasmid was extracted from randomly selected clones, and the sequence was analyzed to confirm the mutation.

Transformants which express the following modified enzymes were thus obtained: Bfu-GDH(G53A), (N176K), N176R, N176E, N176S, (S514G), (S552C), (G53A/S514G), (S514G/S552C), (G53A/S514G/S552C). In addition, multiple mutations which are combinations of S514G, S552C, or the double mutation S514G/S552C with any of the variations (N176K), N176R, N176E, N176S, N225K, N259K, N301K, N326K, N330K, N355K, N487S, T488E, V489I, S490P, N492T, T494A, E495D, A496E, E497K, F499V, D500E, V502L, T504A, A505N were designed, and transformants which express these modified enzymes were created, including the multiple mutants N176K/S490P/D500E/S514G/S552C, N176K/A496E/D500E/S514G/S552C, N176K/S514G/S552C, S514G/S552C, and G53A/S514G/S552C.

Example 6

Productivity of Modified Enzymes and Measurement of Enzyme Activity

Transformants BL21(DE3) for expressing each of the modified enzymes were pre-cultured. Using a 300 mL flask with baffle, 60 mL of Medium A was inoculated with a 1% amount of the transformant, and cultured with shaking at 20° C. and 125 rpm for 28 hours. Next, the cells from 50 mL of the culture were suspended in 5 mL of the BugBuster™ protein-extracting reagent (from Novagen) per gram of wet cells and incubated for 15 minutes at room temperature under gentle shaking. The insoluble fraction was removed by centrifugation (15K rpm, 4° C., 20 minutes), and the supernatant was dialyzed against 20 mM potassium phosphate buffer (pH 6.5) at 4° C. overnight. Following the completion of dialysis, the sample was centrifuged to obtain a supernatant as a partially purified enzyme preparation. The insoluble fraction was suspended at a ratio of 1 mL of the 20 mM potassium phosphate buffer (pH 6.5) to the insoluble fraction from 2 mL of the suspension.

A small-scale expression system was used for several multiple mutation enzymes. Transformants BL21(DE3) for expressing each of the modified enzymes were pre-cultured, and 1 vol % was inoculated on 3 mL of Medium A, and cultured with shaking at 37° C. for 4 hours, and then at 20° C. for 20 hours. Next, the cells from 2 mL of the culture were suspended in 400 μL of BugBuster™, and incubated with shaking at room temperature for 15 minutes. The sample was centrifuged (15,000 rpm, 4° C., 20 minutes) to obtain a supernatant as a partially purified enzyme preparation.

Measurement of the GDH activity was carried out with a DCIP (0.3 mM)/PMS (0.6 mM) system, in 20 mM potassium phosphate buffer (pH 6.5), using glucose (Glc: 1, 2, 4, 10, 20, 40 mM) and xylose (Xyl: 4, 40 mM) as a substrate.

The results are shown in Table 1. Numerical values for specific activity (U/mg) and productivity (U/L) in the table are average values from data from several experiments under the same conditions using 40 mM of glucose as the substrate. Also, using the partially purified enzymes obtained, the correlation between the substrate concentration (glucose: 1, 2, 4, 10, 20, 40 mM) and activity was examined. The Michaelis-Menten constant (Km value) and apparent maximum activity (Vmax) obtained from saturation curves were calculated. It should be noted that the activity values appearing in Tables 1 and 2 of the priority application included some errors in the calculations for determining the activity values from the absorbance data. The correct values are shown in Tables 1 and 2 below.

TABLE 1

|  | U/mg Glc 40 mM | U/L medium Glc 40 mM | Xyl/Glc 4 mM/ 4 mM (%) | Xyl/Glc 40 mM/ 40 mM (%) | Km (mM) | Vmax (U/mg protein) | Vmax/ Km |
| --- | --- | --- | --- | --- | --- | --- | --- |
| Bfu-GDH (WT) | 4.03 | 2710 | 10.9 | 8.1 | 60.3 | 8.7 | 0.14 |
| G53A | 2.75 | 1590 | 5.0 | 5.7 | 81.7 | 8.1 | 0.10 |
| S514G | 11.60 | 7638 | 9.8 | 11.5 | 55.8 | 36.6 | 0.66 |
| S552C | 4.98 | 3023 | 11.2 | 13.5 | 24.0 | 7.8 | 0.33 |
| N176K | 10.75 | 11245 | 12.1 | 10.2 | 54.0 | 25.1 | 0.46 |
| N176R | 12.03 | 12810 | 11.8 | 11.9 | 41.1 | 24.9 | 0.61 |
| N176E | 5.50 | 5443 | 11.9 | 12.2 | 35.6 | 10.4 | 0.29 |
| N176S | 5.98 | 6038 | 11.7 | 11.6 | 36.9 | 11.5 | 0.31 |
| G53A/S514G | 2.78 | 1958 | 5.1 | 5.2 | 84.0 | 8.9 | 0.11 |
| S514G/S552C | 21.60 | 14750 | 13.9 | 12.2 | 20.4 | 27.4 | 1.34 |
| G53A/S514G/S552C | 7.50 | 6423 | 7.4 | 7.9 | 13.8 | 10.1 | 0.74 |
| N176K/S514G/S552C | 34.20 | 22910 | 13.1 | 16.2 | 13.9 | 46.3 | 3.32 |
| N176R/S514G/S552C | 35.10 | 41793 | 14.3 | 16.7 | 17.5 | 61.7 | 3.53 |
| N176E/S514G/S552C | 25.18 | 32585 | 11.7 | 12.4 | 17.6 | 42.0 | 2.38 |
| N176S/S514G/S552C | 20.13 | 27428 | 12.4 | 15.6 | 20.6 | 56.8 | 2.76 |
| G53A/N176K/S514G/ S552C | 31.05 | 19618 | 7.4 | 6.5 | 22.4 | 47.8 | 2.14 |

The mutants N176K, N176R, N176E, N176S, S514G and S552C all showed increased productivity and enzyme activity compared with the control (Bfu-GDH). Even higher productivity and enzyme activity were observed in the double mutant S514G/S552C. Multiple mutants comprising a combination of S514G/S552C with N176K, N176R, N176E and N176S mutants showed very high productivity. The single mutant G53A and the double mutant G53A/S514G showed a productivity similar to that of the control, while the multiple mutant G53A/S514G/S552C exhibited a very high productivity.

The results for multiple mutants containing S514G or S514G/S552C mutation and other mutations are shown in Table 2. Numerical values for specific activity (U/mg) and productivity (U/L) in the table are average values from data for several experiments under the same conditions using 40 mM of glucose as the substrate. Also, the correlation between the substrate concentration (glucose: 1, 2, 4, 10, 20, 40 mM) and the activity was examined using the partially purified enzymes, and the Michaelis-Menten constants (Km value) and apparent maximum activity (Vmax) obtained from saturation curves determined from these results were calculated.

As shown in Table 2, many of the multiple mutants showed a higher productivity than the mutant with a single mutation S514G or with a double mutation S514G/S552C. In particular, very high productivity and enzyme activity were observed for the mutants N176K/S490P/D500E/S514G/S552C, N176K/A496E/D500E/S514G/S552C, N176K/S514G/S552C, S514G/S552C and G53A/S514G/S552C.

The activity of the wild-type enzyme and the mutants with respect to glucose and with respect to xylose were examined. The reactivity of the mutants to xylose was 20% or less, or 15% or less, of the reactivity to glucose, indicating that these enzymes had a high substrate specificity for glucose. The activity of these enzymes to maltose or galactose was not detected.

Additional multiple mutants were similarly created and their activity was measured. In addition, the thermal stability of the enzymes was evaluated by allowing solutions containing the enzymes to stand at 40° C. for 10 minutes, then measuring their residual activity.

TABLE 2

|  | U/mg Glc 40 mM | U/L medium Glc 40 mM | Xyl/Glc 4 mM/ 4 mM (%) | Xyl/Glc 40 mM/ 40 mM (%) | Km (mM) | Vmax (U/mg protein) | Vmax/ Km |
|---|---|---|---|---|---|---|---|
| Bfu-GDH (WT) | 4.03 | 2710 | 10.9 | 8.1 | 60.3 | 8.7 | 0.14 |
| S514G | 11.60 | 7638 | 9.8 | 11.5 | 55.8 | 36.6 | 0.66 |
| S514G/S552C | 21.60 | 14750 | 13.9 | 12.2 | 20.4 | 27.4 | 1.34 |
| N176K/S514G/S552C | 34.20 | 22910 | 13.1 | 16.2 | 13.9 | 46.3 | 3.32 |
| N487S/S514G | 13.73 | 9178 | 10.7 | 8.8 | 78.0 | 41.5 | 0.53 |
| S490P/S514G | 28.40 | 18068 | 9.3 | 9.7 | 35.0 | 53.8 | 1.53 |
| N492T/S514G | 2.48 | 1605 | 8.5 | 9.3 | 28.8 | 4.2 | 0.15 |
| A496E/S514G | 24.38 | 15055 | 8.8 | 8.8 | 49.9 | 55.9 | 1.12 |
| D500E/S514G | 25.30 | 16045 | 9.3 | 9.6 | 48.5 | 56.8 | 1.17 |
| V502L/S514G | 24.40 | 14845 | 10.1 | 9.0 | 48.9 | 55.6 | 1.14 |
| A505N/S514G | 13.88 | 9630 | 7.8 | 8.8 | 47.0 | 30.5 | 0.65 |
| N225K/GC* | 12.80 | 17000 | 10.9 | 16.2 | 21.3 | 35.2 | 1.65 |
| N259K/GC | 13.63 | 16553 | 14.5 | 16.1 | 15.5 | 16.2 | 1.04 |
| N301K/GC | 17.43 | 21753 | 13.3 | 16.0 | 19.3 | 25.9 | 1.34 |
| N326K/GC | 12.85 | 15288 | 14.5 | 15.3 | 23.0 | 30.8 | 1.34 |
| N330K/GC | 20.15 | 23070 | 13.7 | 15.8 | 16.7 | 32.7 | 1.96 |
| N355K/GC | 21.05 | 21655 | 19.7 | 18.0 | 18.7 | 33.4 | 1.79 |
| N487S/GC | 14.00 | 11423 | 10.7 | 13.4 | 23.7 | 22.2 | 0.94 |
| S490P/GC | 25.20 | 16628 | 13.2 | 12.3 | 20.2 | 37.2 | 1.84 |
| N492T/GC | 15.88 | 9378 | 18.1 | 16.7 | 19.7 | 19.1 | 0.97 |
| A495D/GC | 13.23 | 11928 | 13.2 | 16.6 | 15.8 | 18.2 | 1.15 |
| A496E/GC | 22.60 | 15595 | 10.9 | 10.5 | 20.3 | 29.6 | 1.46 |
| D500E/GC | 25.65 | 14838 | 14.1 | 13.3 | 19.0 | 37.0 | 1.95 |
| V502L/GC | 18.73 | 10770 | 14.5 | 16.3 | 18.0 | 19.4 | 1.08 |
| S490P/A496E/GC | 30.40 | 20718 | 11.4 | 13.4 | 16.8 | 44.4 | 2.64 |
| S490P/D500E/GC | 36.20 | 22348 | 12.2 | 12.7 | 14.9 | 50.3 | 3.37 |
| S490P/V502L/GC | 10.55 | 9355 | 14.4 | 20.0 | 15.9 | 13.5 | 0.85 |
| A496E/D500E/GC | 16.30 | 12018 | 12.5 | 16.8 | 15.4 | 21.9 | 1.42 |
| A496E/V502L/GC | 14.95 | 11453 | 13.9 | 18.3 | 13.9 | 19.5 | 1.40 |
| D500E/V502L/GC | 16.05 | 11843 | 15.7 | 18.8 | 13.9 | 21.0 | 1.51 |
| S490P/A496E/D500E/GC | 30.15 | 20910 | 14.5 | 13.3 | 17.5 | 44.2 | 2.52 |
| S490P/A496E/V502L/GC | 11.55 | 8343 | 7.5 | 14.6 | 9.6 | 10.1 | 1.06 |
| S490P/D500E/V502L/GC | 28.60 | 20288 | 14.6 | 14.0 | 15.2 | 39.8 | 2.62 |
| A496E/D500E/V502L/GC | 28.65 | 19475 | 13.4 | 13.5 | 15.6 | 41.5 | 2.65 |
| S490P/A496E/D500E/V502L/GC | 15.30 | 11290 | 15.2 | 20.4 | 13.7 | 19.8 | 1.45 |
| N176K/S490P/D500E/GC | 43.98 | 54780 | 13.5 | 17.7 | 18.1 | 81.3 | 4.50 |
| G53A/N176K/S490P/D500E/GC | 31.78 | 33278 | 7.0 | 7.2 | 23.6 | 48.5 | 2.06 |
| N176K/A496E/D500E/V502L/GC | 45.83 | 39410 | 14.4 | 19.1 | 15.3 | 76.9 | 5.04 |
| G53A/N176K/A496E/D500E/V502L/GC | 26.45 | 31240 | 7.4 | 8.5 | 19.6 | 63.7 | 3.25 |

*GC = S514G/S552C

TABLE 3

| U/mg | Glc 40 mM | 4 mM Xyl/Glc % | 40 mM Xyl/Glc % | Protein mg/ml | U/L medium Glc 40 mM | Km | Vmax | Vmax/Km | Residual activity % 40° C. 10 min |
|---|---|---|---|---|---|---|---|---|---|
| BFU (wild) | 3.49 | 9 | 7.7 | 5.58 | 2,253 | 60.3 | 8.7 | 0.14 | 0 |
| BFU-GC | 17.97 | 14.5 | 13.4 | 6 | 12,159 | 20.4 | 27.4 | 1.34 | 0.2 |
| N176K/GC | 35.76 | 10.4 | 13 | 5.41 | 20,899 | 15.8 | 50.8 | 3.2 | 6.6 |
| N176R/GC | 39.88 | 11.7 | 16.2 | 5.75 | 25,703 | 10 | 50.8 | 5.06 | 8.5 |
| N301E/GC | 17.41 | 12.2 | 13.1 | 5.82 | 11,135 | 18.6 | 26 | 1.4 | 0.1 |
| N225E/GC | 23.08 | 11 | 12.9 | 4.99 | 10,839 | 17.1 | 33.1 | 1.94 | 4 |
| N259K/GC | 11.4 | 10.7 | 14.1 | 5.36 | 6,716 | 15.5 | 16.2 | 1.04 | 3 |
| N259E/GC | 16.88 | 10.2 | 12.8 | 4 | 7,554 | 18.2 | 24.8 | 1.36 | 0.1 |
| N326E/GC | 31.42 | 10.3 | 12.2 | 4.14 | 15,889 | 20.9 | 48.5 | 2.32 | 0.2 |
| N330KGC | 25.45 | 10.2 | 13.1 | 3.85 | 11,939 | 16.9 | 36.5 | 2.16 | 0.3 |
| N330S/GC | 23.27 | 10.3 | 12.6 | 4.54 | 11,628 | 16.7 | 32.7 | 1.96 | 0.2 |
| N355K/GC | 22.82 | 10.5 | 12.2 | 5.49 | 14,024 | 18.7 | 33.4 | 1.79 | 0.2 |
| N355E/GC | 23.25 | 10.1 | 13.5 | 5.00 | 12,078 | 15.5 | 32.9 | 2.12 | 0.2 |
| N492E/GC | 17.27 | 11.4 | 12.3 | 4.56 | 9,137 | 19.6 | 26.0 | 1.33 | 0.1 |

GC: S514G/S552C

As shown in Table 3, multiple mutants of S514G/S552C plus N176K/R, N225E, N326E, N330K/S, or N355K/E showed a high productivity and activity. With regard to thermal stability, about 6 to 8% of residual activity was observed in N176K/R, and about 4% of residual activity was observed in N225E.

Further multiple mutants were constructed by combining various mutations which showed increased activity, and their productivity, activity and stability were examined. The results are shown in Table 4.

the enzymes were about 30,000 U/L, and the apparent Vmax/Km value was also improved. With regard to the stability, the residual activity after 10 minutes of standing in a 40° C. solution was improved to about 10 to 13%.

In addition, combinations of various mutations were created, and their productivity, activity and stability were examined. The multiple mutants shown in Table 5 were found to have particularly high productivity, activity and stability. Among these mutants,

TABLE 4

| U/mg | Glc 40 mM | 4 mM Xyl/Glc % | 40 mM Xyl/Glc % | Protein mg/ml | U/L medium Glc 40 mM | Km | Vmax | Vmax/Km | Residual activity % 40° C. 10 min |
|---|---|---|---|---|---|---|---|---|---|
| N176K/N301K/N330K/GC | 34.04 | 15.0 | 15.5 | 4.30 | 29,334 | 15.8 | 46.8 | 2.97 | 13.0 |
| N176K/N330K/GC | 34.78 | 15.2 | 16.9 | 4.48 | 31,177 | 13.5 | 45.5 | 3.36 | 6.9 |
| N176K/N301K/GC | 34.70 | 15.1 | 16.7 | 4.79 | 33,266 | 13.7 | 46.3 | 3.39 | 3.9 |
| N301K/N330K/GC | 13.21 | 12.2 | 16.8 | 3.70 | 9,791 | 13.9 | 17.1 | 1.23 | 0.3 |
| N176K/N330K/N355K/GC | 27.76 | 13.9 | 17.0 | 4.58 | 25,402 | 13.8 | 36.1 | 2.62 | 6.2 |
| N176K/N225K/N301K/N330K/N355K/GC | 25.08 | 14.0 | 17.7 | 4.07 | 20,399 | 11.4 | 32.4 | 2.84 | 2.6 |
| N176R/N301K/N330K/GC | 33.33 | 15.9 | 16.4 | 5.12 | 34,239 | 14.6 | 44.5 | 3.05 | 11.4 |
| N176R/N225K/N330K/N355K/GC | 21.75 | 11.8 | 18.0 | 4.36 | 18,964 | 11.6 | 27.8 | 2.40 | 6.7 |
| N176R/N225K/N301K/N330K/N355K/GC | 34.46 | 12.4 | 16.6 | 4.79 | 33,033 | 11.4 | 45.0 | 3.94 | 3.7 |
| N176R/N225E/N301K/N326E/N330K/N355E/GC | 34.55 | 13.9 | 16.7 | 4.59 | 31,687 | 11.8 | 45.0 | 3.83 | 12.3 |

GC: S514G/S552C

Of these combinations, the following three multiple mutants exhibited a high productivity and activity, and showed a synergistic effect on stability: N176K/N301K/N330K/S514G/S552C, N176R/N301K/N330K/S514G/S552C and N176R/N225E/N301K/N326E/N330K/N355E/S514G/S552C. The productivity of each of E166R/T168P/N176R/N301K/N330K/S490P/D500E/S514G/S552C exhibited a high Vmax/Km value and a high thermal stability. This enzyme showed a residual activity of 100% after 10 minutes of incubation in a 40° C. solution; with no inactivation observed. Even after 10 minutes at 45° C., up to 40% of residual activity was observed.

TABLE 5

| U/mg | Glc 40 mM | 4 mM Xyl/Glc % | 40 mM Xyl/Glc % | Protein mg/ml | U/L medium Glc 40 mM | Km | Vmax | Vmax/Km | Residual activity % 40° C. 10 min | Residual activity % 45° C. 10 min |
|---|---|---|---|---|---|---|---|---|---|---|
| N176K/S490P/D500E/GC | 46.91 | 11.9 | 15.7 | 7.26 | 45,619 | 13.8 | 64.9 | 4.72 | 24.8 | |
| T168P/GC | 8.05 | 12.0 | 13.3 | 4.07 | 6,551 | 14.9 | 11.1 | 0.74 | 19.6 | |
| E166R/GC | 10.18 | 11.2 | 16.9 | 3.76 | 7,648 | 12.9 | 13.6 | 1.05 | 3.7 | |

TABLE 5-continued

| U/mg | Glc 40 mM | 4 mM Xyl/Glc % | 40 mM Xyl/Glc % | Protein mg/ml | U/L medium Glc 40 mM | Km | Vmax | Vmax/Km | Residual activity % 40° C. 10 min | Residual activity % 45° C. 10 min |
|---|---|---|---|---|---|---|---|---|---|---|
| E166R/T168P/GC | 8.23 | 15.4 | 15.6 | 5.07 | 8,357 | 12.2 | 13.0 | 0.98 | 17.6 | |
| T168P/N176K/S490P/D500E/GC | 55.27 | 12.1 | 15.1 | 7.14 | 44,968 | 14.2 | 73.5 | 5.18 | 63.7 | 1.6 |
| N176K/N301K/N330K/S490P/D500E/GC | 50.17 | 12.5 | 15.7 | 6.80 | 31,393 | 10.5 | 63.7 | 6.08 | 15.1 | 0.3 |
| T168P/N176K/N301K/N330K/S490P/D500E/GC | 47.10 | 11.7 | 15.8 | 7.17 | 36,459 | 11.9 | 61.7 | 5.21 | 50.7 | 1.8 |
| E166R/T168P/N176K/N301K/N330K/PE/GC | 36.18 | 14.1 | 14.2 | 5.28 | 22,938 | 14.9 | 49.8 | 3.35 | 60.8 | 11.3 |
| N176R/N301K/N330K/S490P/D500E/GC | 49.82 | 12.2 | 14.7 | 7.48 | 43,955 | 13.4 | 64.9 | 4.86 | 26.3 | 0.2 |
| T168P/N176R/N301K/N330K/S490P/D500E/GC | 41.11 | 11.9 | 13.9 | 6.91 | 33,519 | 14.4 | 55.2 | 3.83 | 67.7 | 3.2 |
| E166R/T168P/N176R/N301K/N330K/S490P/D500E/GC | 62.67 | 11.7 | 14.7 | 6.40 | 40,092 | 13.1 | 80.6 | 6.15 | 105.5 | 38.5 |
| N163R/T168P/N176R/N301K/N330K/S490P/D500E/GC | 43.96 | 12.4 | 14.8 | 6.59 | 31,877 | 12.3 | 58.5 | 4.74 | 58.0 | 6.7 |
| T168P/N176R/N225E/N301K/N330K/S490P/D500E/GC | 51.16 | 11.3 | 14.9 | 6.80 | 37,576 | 11.7 | 66.2 | 5.64 | 65.8 | 5.3 |
| T168P/N176R/N301K/N330K/S490P/D500E/GC/V556C | 56.18 | 10.9 | 12.8 | 6.43 | 40,486 | 14.9 | 76.9 | 5.18 | 85.8 | 26.9 |

GC: S514G/S552C

Example 7

Introduction of Intramolecular S—S Bonds to Ao-GDH

In order to enhance the thermal stability of the enzyme, a number of mutants were created in which various amino acids on Ao-GDH were substituted with cysteine, and their enzyme activity and thermal stability were investigated. The introduction of mutations and measurement of the enzyme activities were carried out in the same way as in Example 5.

Thermal stability tests were carried out as follows. First, 200 μL of a partially purified enzyme preparation was added and mixed with 800 μL of 20 mM potassium phosphate buffer (pH 6.5) at 45° C., and 100 μL of the mixture was immediately added to 100 μL of 20 mM potassium phosphate buffer (pH 6.5) pre-heated at 45° C. (10-fold dilution at a final concentration). Following addition, the mixture was incubated at 45° C. for 2, 5, 10, 15, 20, 25 or 30 minutes. After the given time had elapsed, the mixture was rapidly cooled in ice. Measurement of the GDH activity was carried out in a DCIP (0.3 mM)/PMS (0.6 mM) system in 20 mM potassium phosphate buffer (pH 6.5) with Glc (40 mM) as the substrate.

Figure 3:
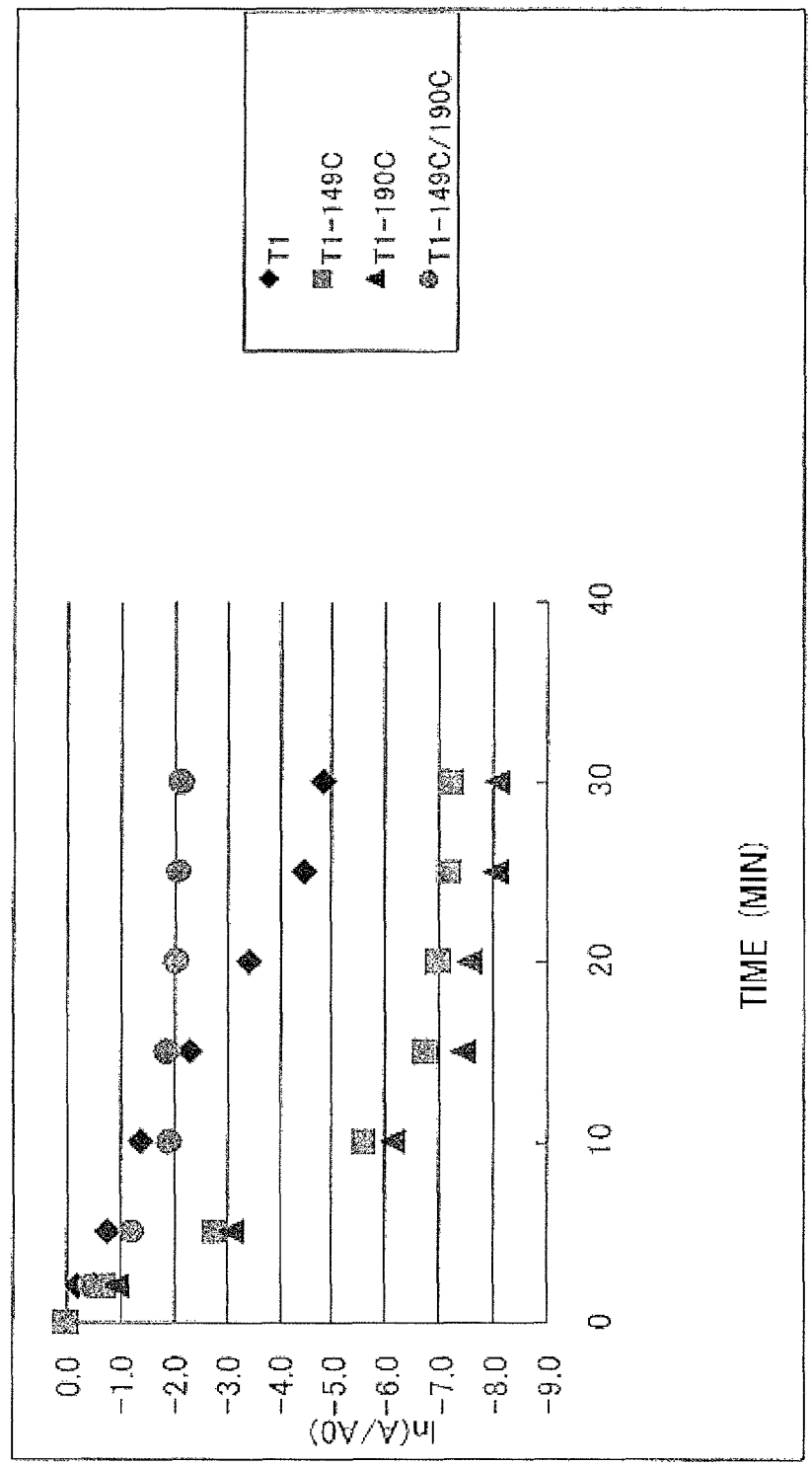

As a result, it was discovered that the modified enzyme in which the amino acid residue V at the position 149 and the amino acid residue G at the position 190 on the FAD-GDH from *Aspergillus oryzae* T1 shown in SEQ ID NO:4 were replaced with cysteine (C) exhibited a particularly high thermal stability and productivity. As shown in FIG. 3, the activity of Ao-GDH decreased with time, while the activity of the V149C/G190C mutant first decreased rapidly to about 30%, then remained constant at about 15%. Because the single mutations of V149C and G190C do not contribute to increased productivity and activity, this improvement in thermal stability is presumed to be due to the formation of S—S bonds within the molecule.

Figure 4:
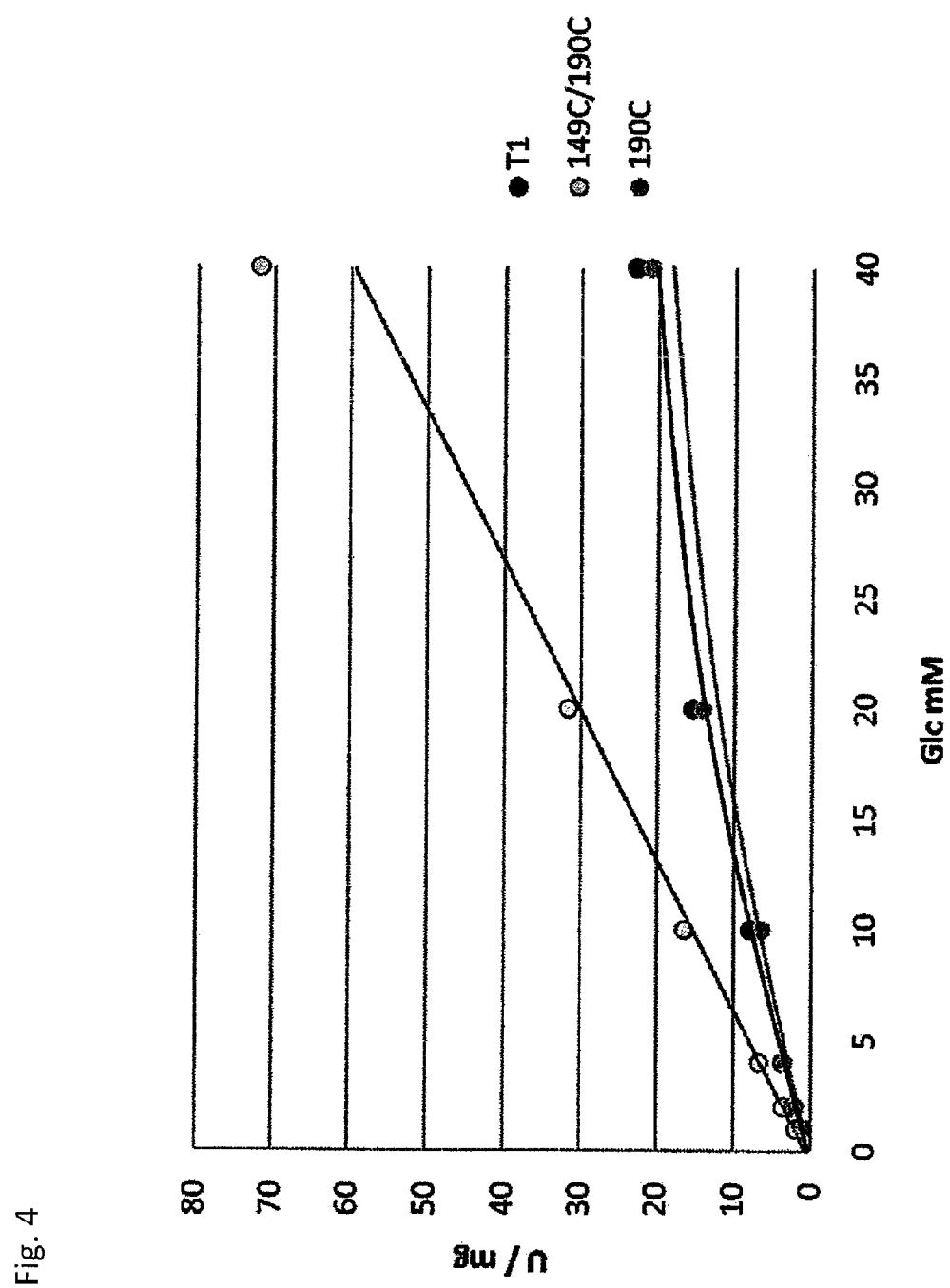
FIG. 4 shows the enzyme activity of wild-type and modified FAD-GDH from *Aspergillus oryzae*.

FIG. 4 shows S-V curves for the wild-type enzyme, V149C/G190C mutated enzyme and the G190C mutated enzyme as a reference. The Km values and the Vmax values are shown in Table 6 below.

TABLE 6

| 20° C./28 h Glc 40 mM | U/mg Glc 40 mM | U/L medium Glc 40 mM | Km (mM) | Vmax (U/mg protein) | Vmax/Km |
|---|---|---|---|---|---|
| Ao-GDH | 57.23 | 30633 | 44.7 | 120.5 | 2.70 |
| V149C | 68.30 | 47303 | 159.9 | 344.8 | 2.16 |
| G190C | 52.33 | 27000 | 51.3 | 119.0 | 2.32 |
| V149C/G190C | 146.55 | 81403 | 140.3 | 625.0 | 4.46 |

It is apparent from these results that the V149C/G190C mutated enzyme also has a high enzyme activity compared with the wild-type enzyme. At present, it is not clear whether the activity was increased by a change in the shape of the substrate pocket due to the formation of intramolecular S—S bonds, or by an apparent improvement in the residual activity of the enzyme due to improvement in the thermal stability.

Example 8

Introduction of Intramolecular S—S Bonds into Bfu-GDH and Other GDHs from Fungi

Based on the results of Example 7, both the amino acid residue A at the position 150 and the amino acid residue T at the position 192 of the FAD-GDH from *Botryotinia fuckeliana* shown in SEQ ID NO:2 were replaced with cysteines (A150C/T190C) to obtain a mutated enzyme. The enzyme was found to have a high thermal stability. In addition, multiple mutants were created by combining this mutation with some of the mutations that showed high productivity in Example 6, and the enzyme activity and thermal stability were similarly evaluated.

Figure 5:
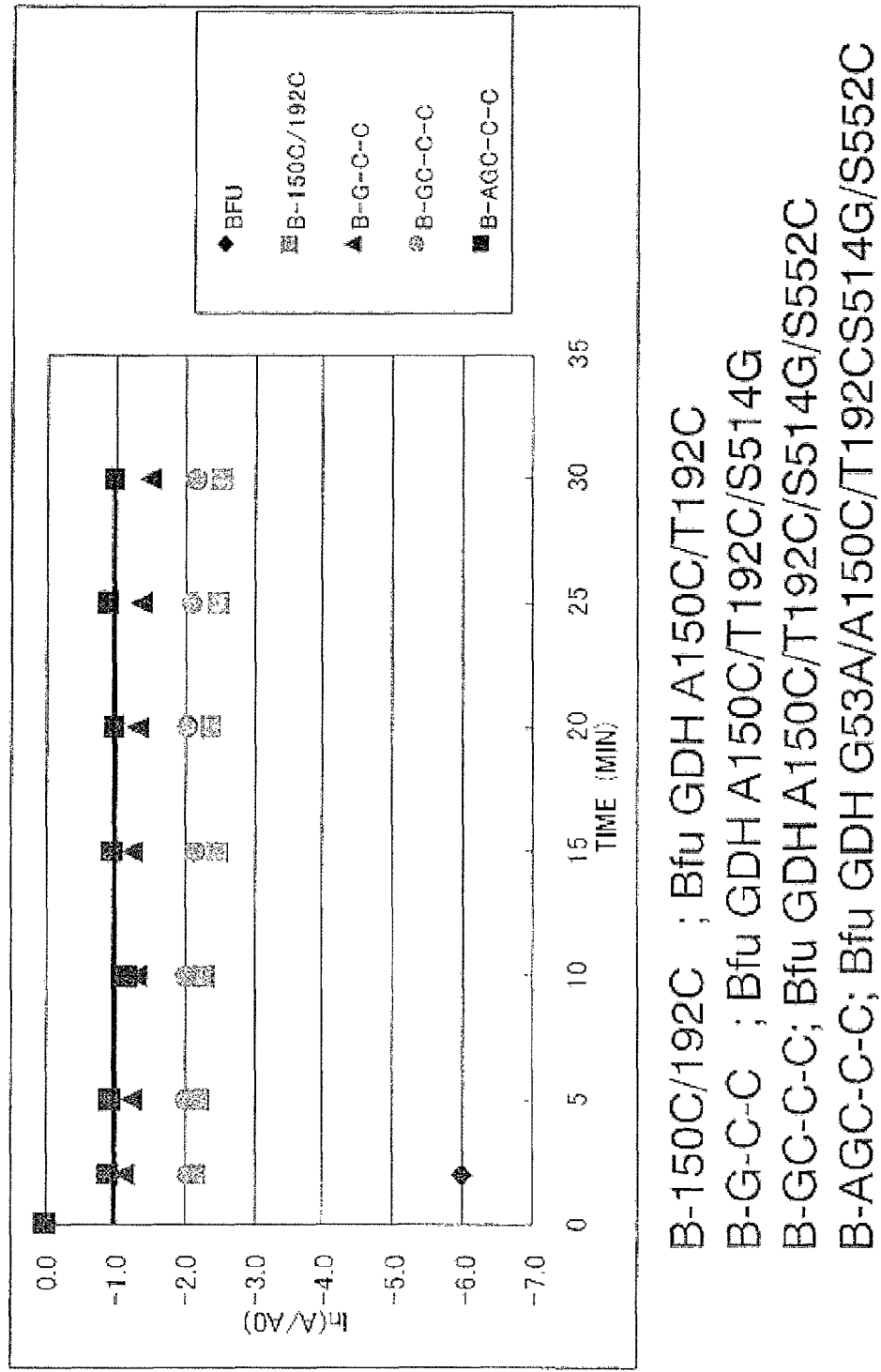
FIG. 5 shows the thermal stability of wild-type and modified FAD-GDH from *Botryotinia fuckeliana*.

FIG. 5 shows the thermal stability of A150C/T192C mutant of Bfu-GDH. When the A150C/T192C mutation or multiple mutations including A150C/T192C were introduced to Bfu-GDH, the enzyme activity remained the same or decreased, while the thermal stability was increased. After heat treatment at 45° C., the activity was decreased immediately thereafter, but subsequently the decreasing rate slowed. Introduction of these mutations had no apparent effect on the glucose/xylose selectivity.

In addition, genes coding for *Scienotinia sclerotiorum* and *Aspergillus niger* 40715 glucose dehydrogenases and having the sequences shown in FIG. 1 were synthesized (SEQ ID NO:7 and SEQ ID NO:8, respectively), and expressed in *E. coli*. Also mutated enzymes containing the A150C/T191C or Y150C/G191C mutation was created, and the enzyme activity and thermal stability were similarly evaluated.

Table 7 shows the thermal stability of the mutants thus created, which is expressed as the inactivation rate constant (k (min$^{-1}$)) obtained from an inactivation curve over a given period of time and as the half-life ($t_{1/2}$ (min)).

TABLE 7

Thermal Stability of Wild-Type and Mutated Glucose Dehydrogenases

| | Mutation | Measurement time (min) | k (min−1) | t½ (min) |
|---|---|---|---|---|
| Ao-GDH | Wild-type | 0-30 | 1.7 × 10−1 | 4.1 |
| | V149C/G190C | 15-30 | 1.7 × 10−2 | 39.8 |
| Bfu-GDH | Wild-type | 0-2 | 3.0 | 0.2 |
| | A150C/T192C | 2-30 | 1.3 × 10−2 | 53.3 |
| | A150C/T192C/ S514G | 2-30 | 4.2 × 10−3 | 165.0 |
| | A150C/T192C/ S514G/S552C | 2-30 | 1.0 × 10−2 | 67.3 |
| | G53A/A150C/ T192C/S514G/ S552C | 2-30 | 2.0 × 10−4 | 3465.7 |
| S. sclerotiorum GDH | Wild-type | 0-5 | 4.1 × 10−1 | 1.7 |
| | A150C/T191C | 5-30 | 3.9 × 10−3 | 177.7 |
| A. nigar 40715 GDH | Wild-type | 0-2 | 8.4 × 10−1 | 0.8 |
| | Y150C/G191C | 10-15 | 3.9 × 10−2 | 18.0 |

Example 9

Fabrication and Evaluation of Enzyme Sensor

Enzyme electrodes were fabricated using the *Aspergillus oryzae* T1-derived V149C/G190C mutated enzyme and the *Botryotinia fuckeliana*-derived S514G/S552C mutated enzyme. Carbon paste (20 mg) was added to 5 units of the modified FAD-GDH of the invention and freeze-dried. The mixture was thoroughly mixed and filled only onto the surface of a carbon paste electrode on which about 40 mg of carbon paste had already been filled, and abraded on filter paper. The electrode was treated with 10 mM MOPS buffer (pH 7.0) containing 1% glutaraldehyde at room temperature for 30 minutes, then with 10 mM MOPS buffer (pH 7.0) containing 20 mM of lysine at room temperature for 20 minutes, thereby blocking the free aldehyde groups. This electrode was equilibrated in the 10 mM MOPS buffer (pH 7.0) at room temperature for at least 1 hour. The electrode was stored at 4° C.

Measurement of the glucose concentration was carried out using the enzyme sensor thus fabricated. Using enzyme sensors having the modified FAD-GDHs of the invention immobilized thereon, glucose was able to be measured in a concentration range of from 0.1 to 5 mM.

INDUSTRIAL APPLICABILITY

The present invention is useful for measuring glucose concentration, and particularly for measuring a blood sugar level.

The invention claimed is:

1. A protein comprising the amino acid sequence set forth in SEQ ID NO:2, wherein the protein has amino acid mutations selected from the group consisting of A150C/T192C, N176K/S490P/D500E/S514G/S552C, N176K/A496E/D500E/S514G/S552C, N176K/S514G/S552C, S514G/S552C G53A/S514G/S552C, N176K/N301K/N330K/S514G/S552C, N176R/N301K/N330K/S514G/S552C, N176R/N225E/N301K/N326E/N330K/N355E/S514G/S552C, and E166R/T168P/N176R/N301K/N330K/S490P/D500E/S514G/S552C.

2. A protein comprising the amino acid sequence set forth in SEQ ID NO:4, wherein the protein has the amino acid mutations V149C and G190C.

3. A glucose dehydrogenase of fungal origin, having an amino acid sequence selected from the group consisting of SEQ ID NO:2 and SEQ ID NOs: 5 to 9, wherein both amino acids at the positions corresponding to V149 and G190 on the amino acid sequence of SEQ ID NO:4 are substituted with cysteine.

4. A gene coding for the protein of anyone of claims 1, 2 and 3.

5. A recombinant vector comprising the gene of claim 4.

6. A transformant or transductant obtained by transformation with the recombinant vector of claim 5.

7. A method of producing glucose dehydrogenase comprising culturing the transformant of claim 6, and collecting glucose dehydrogenase from the culture.

8. A method of analyzing glucose comprising measuring the concentration of glucose in a sample using the protein of any one of claims 1, 2 and 3.

9. A glucose assay kit comprising the protein of any one of claims 1, 2 and 3.

10. An enzyme electrode comprising the protein according to any one of claims 1, 2 and 3 immobilized on the surface of the electrode.

11. The enzyme electrode according to claim 10, further comprising a glucose sensor as a working electrode.

* * * * *